(12) United States Patent
Chung

(10) Patent No.: US 11,517,730 B2
(45) Date of Patent: Dec. 6, 2022

(54) HEMOSTASIS VALVE DEVICE

(71) Applicant: HuBioMed Inc., Gyeonggi-do (KR)

(72) Inventor: Sun Chung, Gyeonggi-do (KR)

(73) Assignee: HuBioMed Inc., Gyeonggi-do (KR)

( * ) Notice: Subject to any disclaimer, the term of this patent is extended or adjusted under 35 U.S.C. 154(b) by 468 days.

(21) Appl. No.: 16/693,820

(22) Filed: Nov. 25, 2019

(65) Prior Publication Data

US 2020/0171293 A1 Jun. 4, 2020

(30) Foreign Application Priority Data

Nov. 30, 2018 (KR) ........................ 10-2018-0152644

(51) Int. Cl.
| | |
|---|---|
| *A61M 39/06* | (2006.01) |
| *A61M 5/36* | (2006.01) |
| *A61M 39/10* | (2006.01) |
| *A61M 39/20* | (2006.01) |

(52) U.S. Cl.
CPC .............. *A61M 39/06* (2013.01); *A61M 5/36* (2013.01); *A61M 39/0613* (2013.01); *A61M 39/105* (2013.01); *A61M 39/20* (2013.01); *A61M 2039/062* (2013.01); *A61M 2039/0633* (2013.01); *A61M 2039/0673* (2013.01); *A61M 2039/205* (2013.01)

(58) Field of Classification Search
CPC .......... A61M 39/06; A61M 2039/0673; A61M 2039/062; A61M 2039/0633; A61M 39/20; A61M 39/0613; A61M 5/36
See application file for complete search history.

(56) References Cited

U.S. PATENT DOCUMENTS

| | | | |
|---|---|---|---|
| 2002/0049423 A1* | 4/2002 | Howell | A61M 25/01 604/528 |
| 2006/0089604 A1* | 4/2006 | Guerrero | A61M 5/1408 604/247 |
| 2010/0057004 A1* | 3/2010 | Christensen | A61M 39/22 604/122 |

(Continued)

FOREIGN PATENT DOCUMENTS

| | | |
|---|---|---|
| JP | 2010-505548 A | 2/2010 |
| JP | 2017-148561 A | 8/2017 |

(Continued)

*Primary Examiner* — Jenna Zhang
(74) *Attorney, Agent, or Firm* — Harness, Dickey & Pierce, P.L.C.

(57) ABSTRACT

Disclosed is a hemostasis valve device including a connector including a first channel, a holder disposed at a first end of the connector and configured to communicate with the first channel, and a valve portion disposed at a second end of the connector and configured to selectively open or close the first channel. Here, the connector includes a first pipe including the first channel and a second pipe which diverges from a first point of the first pipe and includes a second channel configured to communicate with the first channel. Also, the first pipe includes a hole which allows the first channel to communicate with the outside. Here, the hemostasis valve device further includes an opening and closing portion disposed at the first pipe and configured to selectively open or close the hole. The hole is disposed between the first end and the first point.

8 Claims, 34 Drawing Sheets

(56) References Cited

U.S. PATENT DOCUMENTS

2014/0194831 A1* 7/2014 Chung .............. A61M 39/0613
                                                               604/246
2014/0207083 A1* 7/2014 Pessin ............... A61M 39/0606
                                                               604/256

FOREIGN PATENT DOCUMENTS

JP       2018-009653 A    1/2018
KR   10-2001-0022303 A    3/2001

* cited by examiner

HEMOSTASIS VALVE DEVICE

CROSS-REFERENCE TO RELATED APPLICATION

This application claims priority to and the benefit of Korean Patent Application No. 10-2018-0152644, filed on Nov. 30, 2018, the disclosure of which is incorporated herein by reference in its entirety.

FIELD

Embodiments relate to a hemostasis valve device.

BACKGROUND

Hemostasis valve devices are devices for introducing an introducer, a guide wire, or catheter (hereinafter, referred to as catheters) into blood vessels. Hemostasis valve devices guide catheters to be precisely inserted into coronary arteries or veins when cardiovascular angiography, percutaneous transluminal coronary angioplasty, or the like is performed. Also, hemostasis valve devices prevent blood from flowing backward through coronary arteries or veins. Medications may be injected through hemostasis valve devices as necessary.

As one of hemostasis valve devices, Korean Patent Publication No. 10-2001-0022303 (published on Mar. 15, 2001, hereinafter, referred to as the document) discloses a configuration contracted and extended according to according to rotation of a cap. However, the hemostasis valve device disclosed in the document has a problem that air flows into blood vessels when catheters are inserted into coronary arteries or veins. For example, bubbles may form in a contrast medium. Otherwise, bubbles may form during a process of injecting a contrast medium. When air flows into blood vessels, air embolism that bubbles block blood vessels may be caused. When air flows into blood vessels of a patient as described above, it may be fatal to the life of the patient. When bubbles block blood vessels connected to the heart or block cerebrovascular blood vessels, the patient may be led to death due to a cardiac arrest, a cerebral hemorrhage, or the like.

Accordingly, practitioners should pay a lot of attention to prevent air from flowing into blood vessels when catheters are inserted or medications are injected into coronary arteries or veins. Accordingly, a fatigue level of practitioners is high and a lot of skilled practitioners are necessary. Above all, a possibility of succeeding in treatment is significantly low.

RELATED ART DOCUMENT

[Patent Document]
(Patent Document 0001) Korean Patent Publication No. 10-2001-0022303 (published on Mar. 15, 2001)

SUMMARY

The present invention is directed to providing a hemostasis valve device configured to prevent air from flowing into blood vessels.

Aspects of the present invention are not limited to the above-stated aspect and other unstated aspects of the present invention will be understood by those skilled in the art from a following description.

According to an aspect of the present invention, there is provided a hemostasis valve device including a connector including a first channel, a holder disposed at a first end of the connector and configured to communicate with the first channel, and a valve portion disposed at a second end of the connector and configured to selectively open or close the first channel. Here, the connector includes a first pipe including the first channel and a second pipe which diverges from a first point of the first pipe and includes a second channel configured to communicate with the first channel. Also, the first pipe includes a hole which allows the first channel to communicate with the outside. Here, the hemostasis valve device further includes an opening and closing portion disposed at the first pipe and configured to selectively open or close the hole. The hole is disposed between the first end and the first point. The connector may include a deaeration pipe including the hole. Here, the opening and closing portion may include a sealing member disposed on the deaeration pipe and configured to cover the hole and a first member disposed above the sealing member and coupled with the deaeration pipe to be vertically movable. The first member may include a tube which protrudes downward and communicates with the outside. The sealing member may include an incised portion, and the tube may communicate with the hole while passing through the incised portion.

The opening and closing portion may further include a second member which is coupled with the deaeration pipe and includes a hole through which the tube passes and an elastic member. Here, the first member may be coupled with the second member to be vertically movable. The first member may be disposed above the second member, and the elastic member may be disposed between the first member and the second member.

The first member may include a top surface and a side surface, and the first member may further include a connection hole which connects the side surface with the tube.

The connector may include a deaeration pipe including the hole. Here, the opening and closing portion may include a sealing member which is disposed on the deaeration pipe and includes the hole, a first member coupled with the deaeration pipe, and a second member rotatably coupled with the first member. The first member may include a discharge hole which communicates with the outside. The second member may include a connection hole. The connection hole may communicate with the hole, and the connection hole and the discharge hole may selectively communicate with each other according to rotation of the second member.

The sealing member may include a first part disposed inside the deaeration pipe and a second part extending from the first part and disposed on a top surface of the deaeration pipe. Also, the second part may come into contact with an inner surface of the first member.

The first member may be rotatably fastened to an outer surface of the deaeration pipe, and the first member may include a plurality of ribs protruding from an outer surface thereof.

The connector may include a deaeration pipe including the hole. Here, the opening and closing portion may include a sealing member disposed on the deaeration pipe and including the hole and a first member slidably coupled with the connector. Also, the first member may slide and may selectively open or close the hole.

The connector may include a pair of guides protruding from a surface of the connector and disposed with the deaeration pipe therebetween. Also, the first member may include a body coming into contact with the guides and is disposed at the body in an elastically deformable cantilever form.

The hemostasis valve device may include a first protrusion formed on a bottom surface of the cover, coming into contact with the sealing member, and located inside the hole.

The guides may include stoppers, and the body may include second protrusions held by the stoppers.

The connector may include a deaeration pipe including the hole. Here, the opening and closing portion may include a first member pivotably coupled with the deaeration pipe and a sealing member disposed on the first member. Also, the first member may selectively cover the hole by pivoting of the first member on the deaeration pipe.

The sealing member may be selectively disposed inside the hole by pivoting of the first member on the deaeration pipe.

The first member may include a hole, and the deaeration pipe may include a protrusion disposed in the hole.

The connector may include a deaeration pipe including the hole. Here, the opening and closing portion may include a sealing member coupled with the deaeration pipe and covering the hole and a first member coupled with the deaeration pipe and covering the sealing member. Also, the first member may include a through hole which exposes the sealing member.

The deaeration pipe may include a first protrusion protruding from a side surface of the deaeration pipe and a second protrusion protruding from a top surface of the deaeration pipe. Here, the first member may include a first groove in which the first protrusion is disposed, and the sealing member may include a second groove in which the second protrusion is disposed.

The first member may come into contact with the deaeration pipe and the sealing member.

According to another aspect of the present invention, there is provided a hemostasis valve device including a connector which includes a first pipe and a second pipe diverging from a first point of the first pipe, a holder disposed at a first end of the first pipe, and a valve portion disposed at a second end of the first pipe. Here, the first pipe includes a deaeration pipe in which a hole is disposed. The hemostasis valve device further includes an opening and closing portion disposed at the deaeration pipe and configured to selectively open or close the hole. The hole is disposed between the first end and the first point.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION

The aspects, particular advantages, and novel features of the present invention will become apparent from a detailed description of exemplary embodiments with reference to the attached drawings. Also, the terms used in the specification and the claims should not be limited to general or lexical meanings and should be interpreted as meanings and concepts coinciding with the technical concept of the present invention on the basis of a principle in which the inventor can appropriately define the concept of the terms to describe the invention in the best manner. Also, in a description of the present invention, a detailed description of well-known functions or components of the related art will be omitted when it is deemed to obscure the essence of the present invention.

Figure 1:
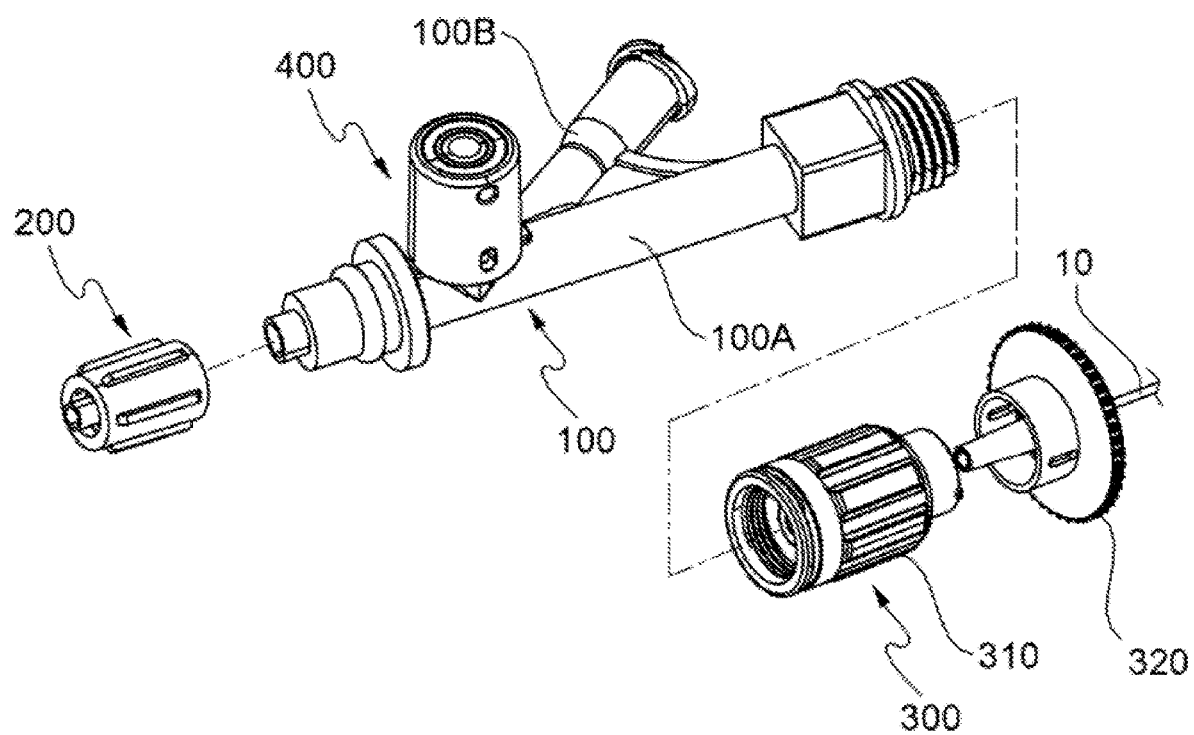
FIG. 1 is a view of a hemostasis valve device according to an embodiment.

FIG. 1 is a view of a hemostasis valve device according to an embodiment.

Referring to FIG. 1, a hemostasis valve device according to an embodiment may include a connector 100, a holder 200, a valve portion 300, and an opening and closing portion 400. The holder 200 is disposed at one end of the connector 100. The valve portion 300 is disposed at another end of the connector 100. The opening and closing portion 400 is disposed between the one end and the other end of the connector 100.

The connector 100 is a tubular member. The connector 100 may include a first pipe 100A and a second pipe 100b. The second pipe 100b diverges from the first pipe 100A. Here, a plurality of such second pipes 100b may be present. Catheters 10 may be introduced through the first pipe 100A. Medications may flow through the second pipe 100b. The holder 200 is connected to a hose (not shown). The holder 200 connects the hose to the first pipe 100A. The holder 200 allows the hose and the first pipe 100A to communicate with each other. The holder 200 may be rotationally fastened to the first pipe 100A. The valve portion 300 is a place configured to supply the catheters 10. The catheters 100 are inserted into the valve portion 300. The catheters 10 inserted in the valve portion 300 passes through the first pipe 100A and the holder 200 and is inserted into the hose. The valve portion 300 performs a function of sealing a channel of the connector 100 by selectively tightening an inlet through which the catheters 10 are inserted while supplying the catheters 10 to the first pipe 100A.

The connector 100 may be formed of a transparent material to allow a user to see bubbles in the channel with naked eyes.

The valve portion 300 configured to selectively tighten the inlet through which the catheters 10 are inserted while supplying the catheters 10 to the connector 100 may have a variety of shapes. For example, the valve portion 300 may be divided into a body 310 and a handle 320. The body 310 is connected to the connector 100. The handle 320 may be fastened to the body 310 to be vertically movable. The body 310 may be rotationally fastened to the connector 100. Although not shown in the drawing, sealing members in which through holes through which the catheters 10 pass are arranged may be arranged inside the body 310. When the handle 320 vertically moves or the body 310 rotates, the sealing members vary in form while being pressurized or released such that the through holes through which the catheters 10 pass are extended or contracted.

Figure 2:
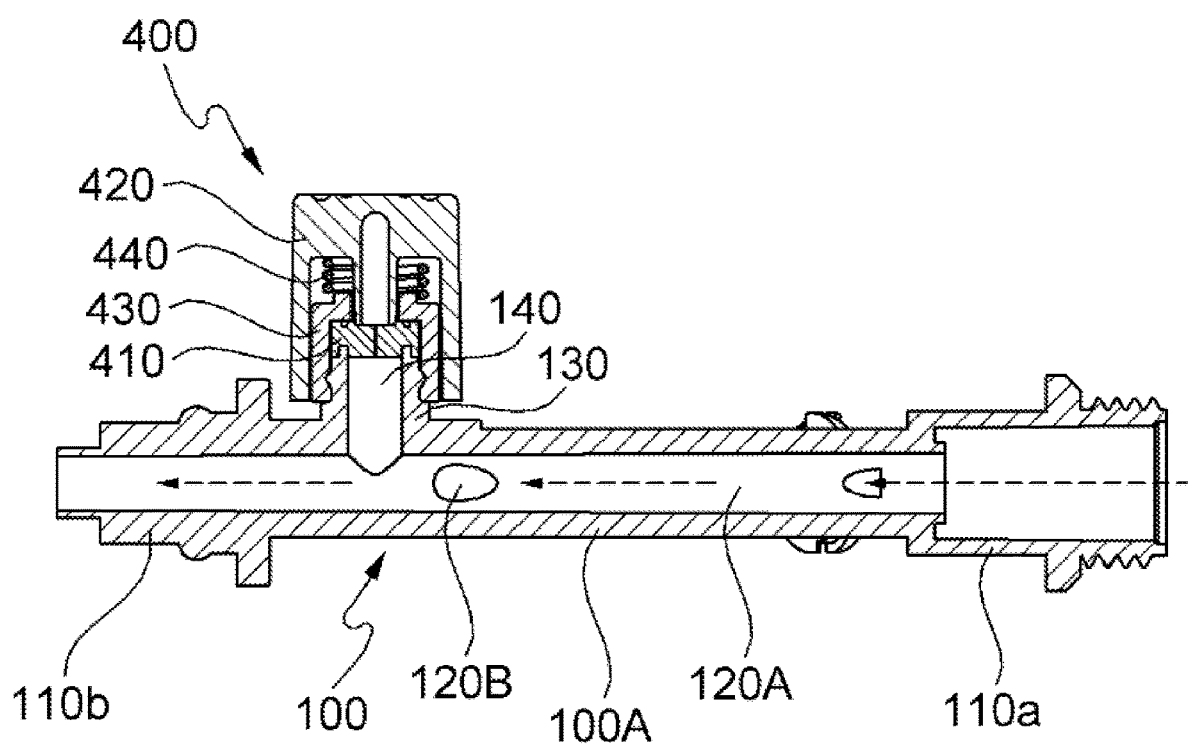
FIG. 2 is a side cross-sectional view illustrating a connector and an opening and closing portion shown in FIG. 1.

FIG. 2 is a side cross-sectional view illustrating the connector 100 and the opening and closing portion 400 shown in FIG. 1.

Referring to FIG. 2, the first pipe 100A may include a first end portion 110a and a second end portion 110b. The first end portion 110a is disposed on one side of the first pipe 100A, and the second end portion 110b is disposed on the other side of the first pipe 100A. The valve portion 300 is connected to the first end portion 110a. The holder 200 is connected to the second end portion 110b. The first pipe 100A includes a first channel 120A therein. The catheters 10 may be supplied through the first channel 120A. The first pipe 100A may include a deaeration pipe 130. The deaeration pipe 130 includes a hole 140. The hole 140 communicates with the first channel 120A. The hole 140 may diverge from the first channel 120A. The deaeration pipe 130 is configured to discharge bubbles existing in the first channel 120A outwards. The deaeration pipe 130 may protrude from the first pipe 100A.

The opening and closing portion 400 may be disposed at the deaeration pipe 130. The opening and closing portion 400 selectively opens the hole 140. When the opening and closing portion 400 opens the hold 140, bubbles existing in the first channel 120A may be discharged outward through the hole 140. Since a pressure in the first channel 120A, particularly, a pressure at the second end portion 110b connected to a blood vessel of a patient is higher than atmospheric pressure, bubbles existing in the first channel 120A do not flow toward the second end portion 110b and are introduced to the hole 140 and discharged outward. The opening and closing portion 400 may be operated by a user's operation such as pushing, pulling, turning, and the like. The opening and closing portion 400 of the hemostasis valve device according to the embodiment is operated by a simple operation of the user. This significantly enhances repetitiveness and easiness of a bubble removal operation during a treatment process.

A variety of embodiments of the opening and closing portion 400 may be present according to methods of operating the same.

Figure 3:
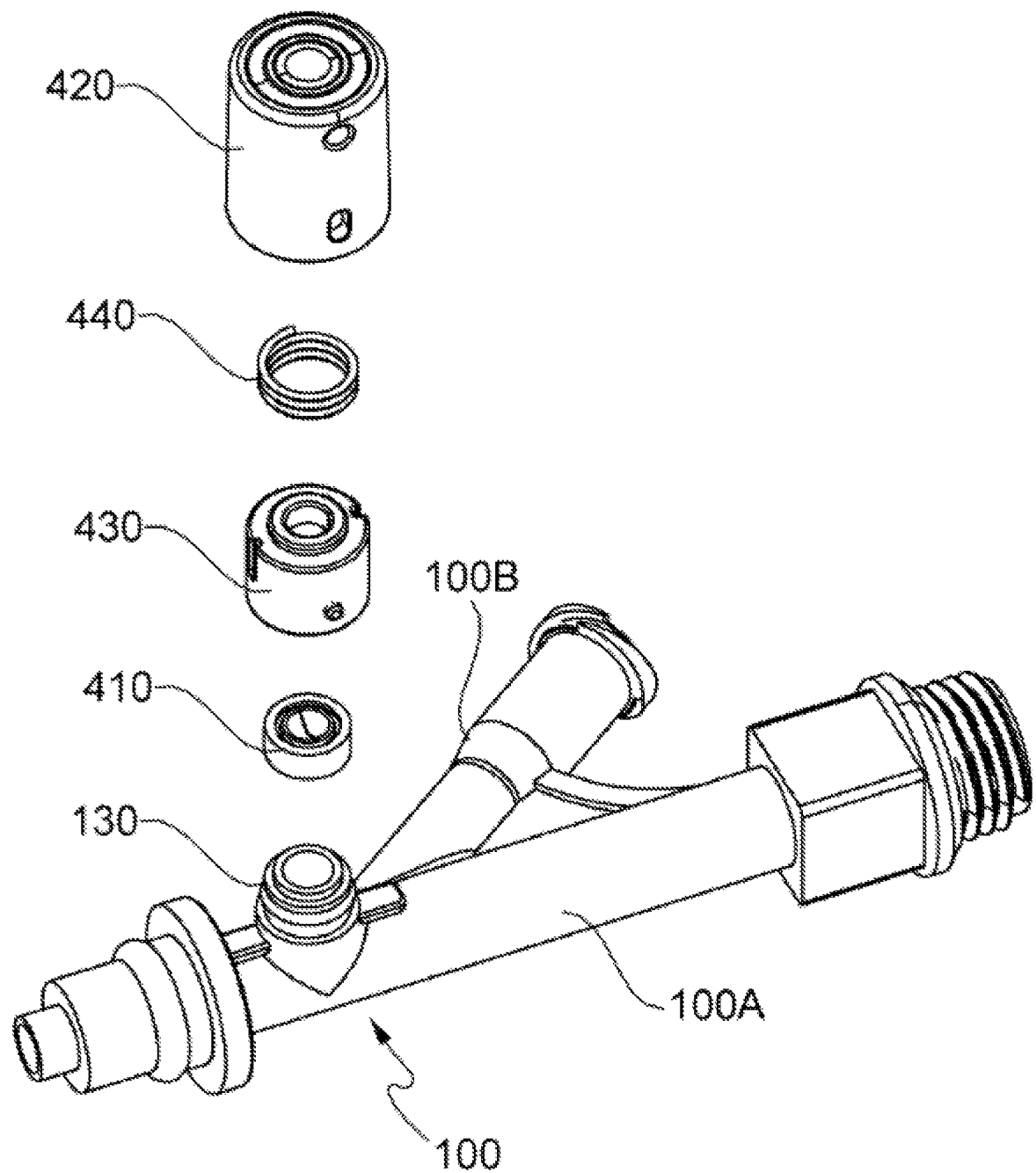
FIG. 3 is an exploded perspective view illustrating the opening and closing portion.

FIG. 3 is an exploded perspective view illustrating the opening and closing portion 400.

As an example, the opening and closing portion 400 may be operated by a pushing operation of the user.

Referring to FIGS. 2 and 3, the opening and closing portion 400 may include a sealing member 410, a first member 420, a second member 430, and an elastic member 440. The sealing member 410 may be disposed at a top end of the deaeration pipe 130. The sealing member 410 covers the hole 140. The first member 420 may be disposed outside the sealing member 410. The second member 430 may be disposed between the first member 420 and the sealing member 410. The elastic member 440 may be disposed between the first member 420 and the second member 430.

Figure 4:
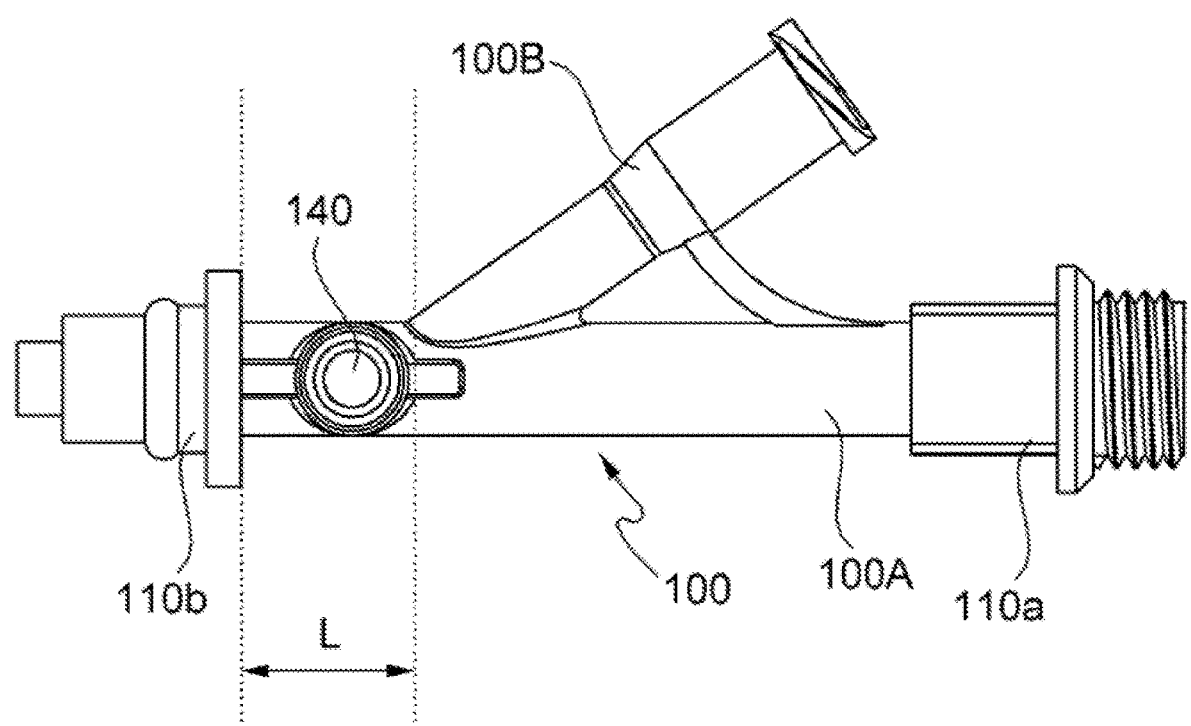
FIG. 4 is a view illustrating a position of a hole.

FIG. 4 is a view illustrating a position of the hole 140.

Referring to FIG. 4, the hole 140 may be disposed in a first section L. The first section L corresponds to a space between the first end portion 110b and a first point. The first point indicates a point at which the second pipe 100B diverges from the first pipe 100A. Bubbles included in medications or bubbles caused by injection of medications join the first channel 120. Accordingly, it is necessary to dispose the hole 140 in the first section L in order to remove not only bubbles caused by injection of the catheters 10 but also bubbles included in medications or bubbles caused by injection of medications.

Figure 5:
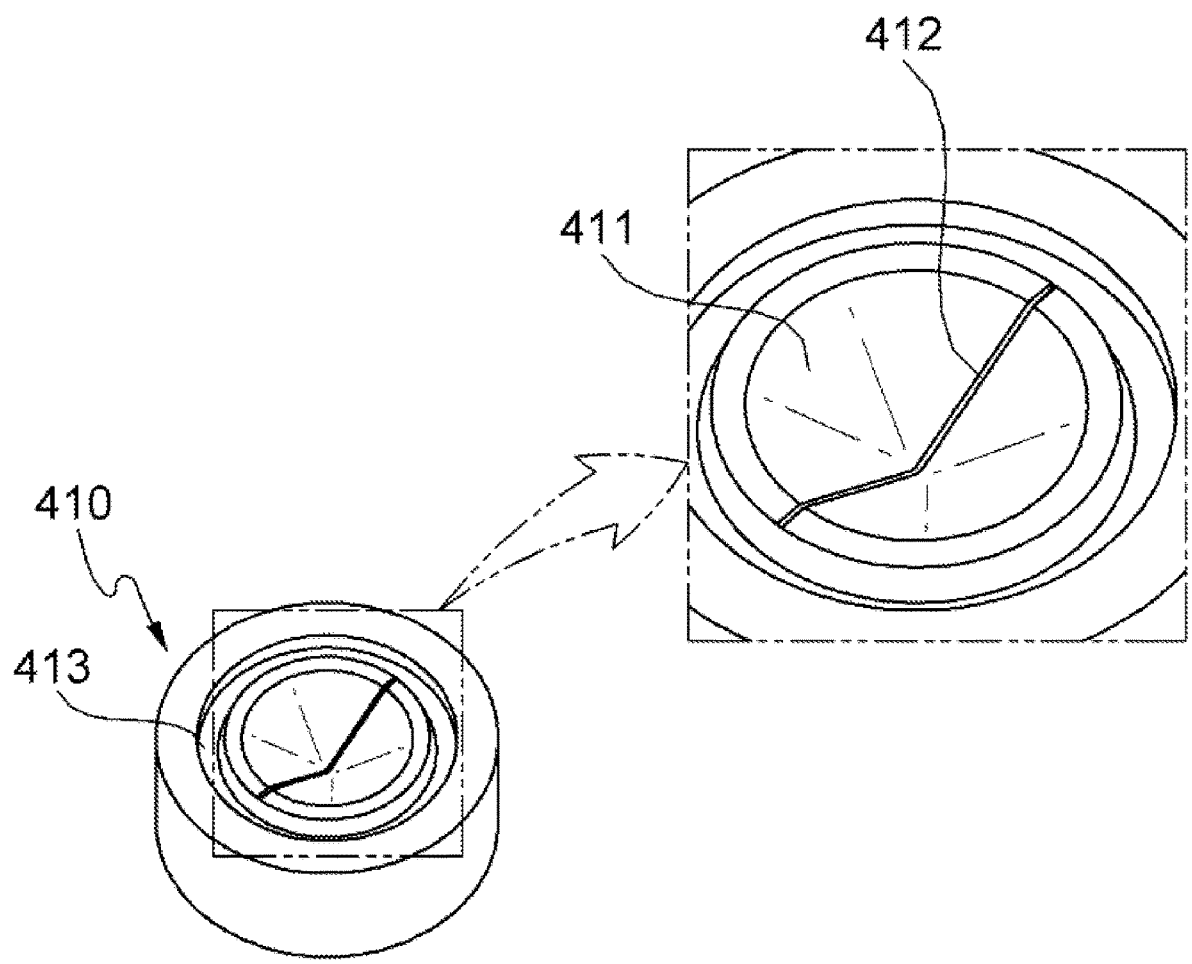
FIG. 5 is a perspective view illustrating a sealing member.
Figure 6:
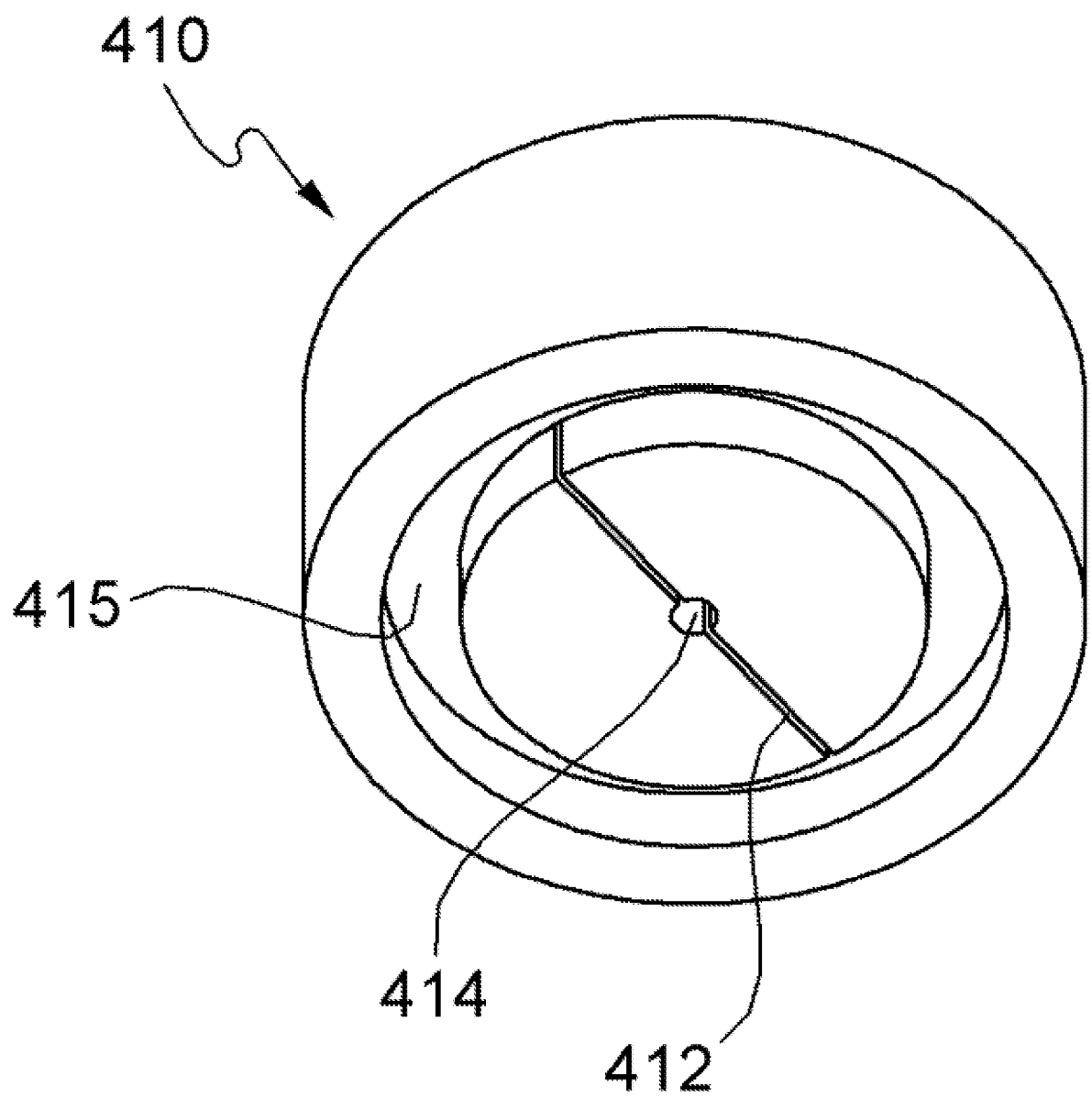
FIG. 6 is a bottom view illustrating the sealing member.

FIG. 5 is a perspective view illustrating the sealing member 410, and FIG. 6 is a bottom view illustrating the sealing member 410.

Referring to FIGS. 5 and 6, the sealing member 410 directly opens or closes the hole 140. The sealing member 410 may be a cylindrical member. A concave groove 411 may be disposed at a top surface of the sealing member 410. The groove 411 may have a conical shape. The sealing member 410 may include an incised portion 412. In the drawings, a shape of the incised portion 412 is shown as a straight line as an example. However, the present invention is not limited thereto, and the incised portion 412 may be implemented to have a variety of shapes such as a cross shape, a star shape, and the like. The conical groove 411 allows the incised portion 412 to easily extend. The incised portion 412 may be disposed across the groove 411. An extension area 414 of the incised portion 412 may be disposed at a center of a bottom surface of the sealing member 410. An annular first groove 413 may be disposed at the top surface of the sealing member 410. The annular first groove 413 is configured to be coupled with the second member 430. The first groove 413 enhances a coupling property and adhesion between the second member 430 and the sealing member 410.

An annular second groove 415 may be disposed at a bottom surface of the sealing member 410. The annular second groove 415 is configured to be coupled with a top surface of the deaeration pipe 130. The second groove 415 enhances a coupling property and adhesion between the deaeration pipe 130 and the sealing member 410.

The sealing member 410 is formed of an elastic material. When an external force is applied to the sealing member 410, the sealing member 410 is deformed. When the sealing member 410 is deformed, the incised portion 412 extends or contracts. When the incised portion 412 extends, the hole 140 is opened. On the other hand, when the incised portion 412 contracts, the hole 140 is closed. When the incised portion 412 extends, bubbles existing in the hole 140 may be disposed outside the deaeration pipe 130. When the sealing member 410 is deformed, the extension area 414 of the incised portion 412 extends to be greater than the incised portion 412 such that bubbles in the hole 140 may be induced to more easily pass through the sealing member 410.

Figure 7:
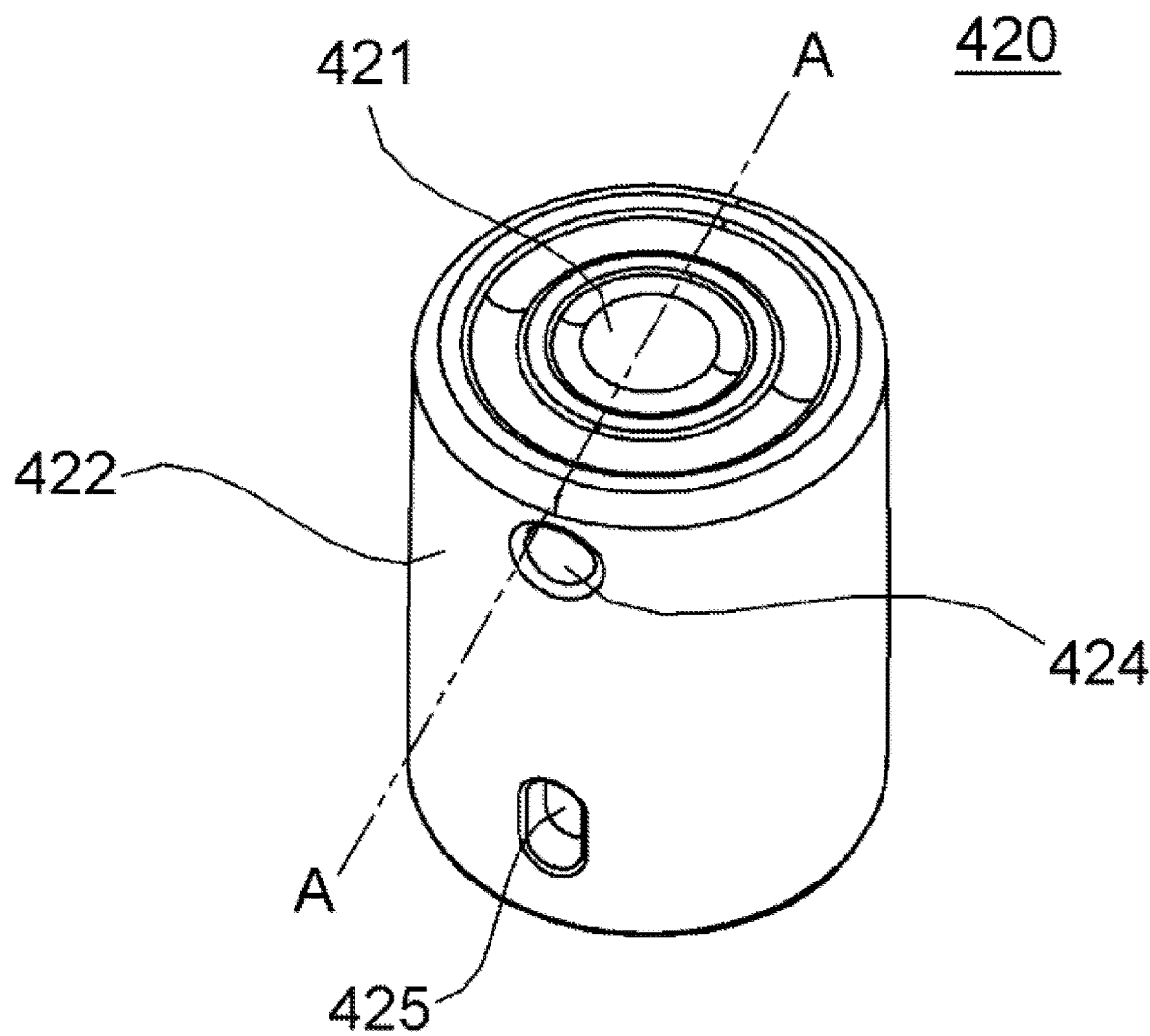
FIG. 7 is a perspective view illustrating a first member shown in FIG. 4.
Figure 8:
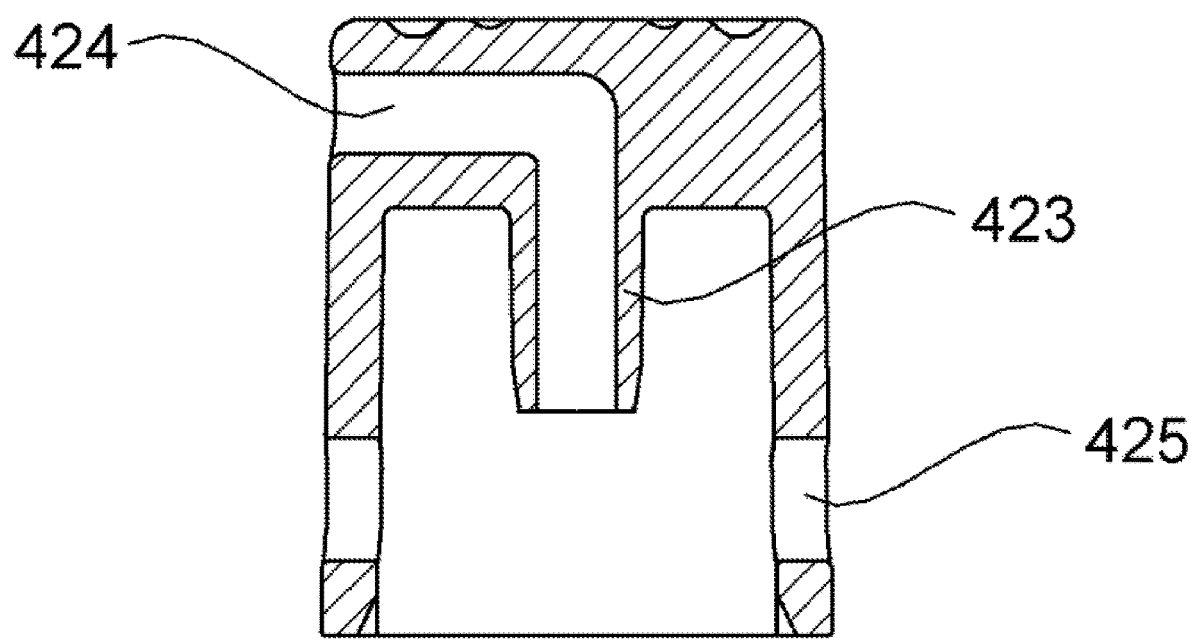
FIG. 8 is a cross-sectional view illustrating the first member taken along line A-A of FIG. 7.
Figure 9:
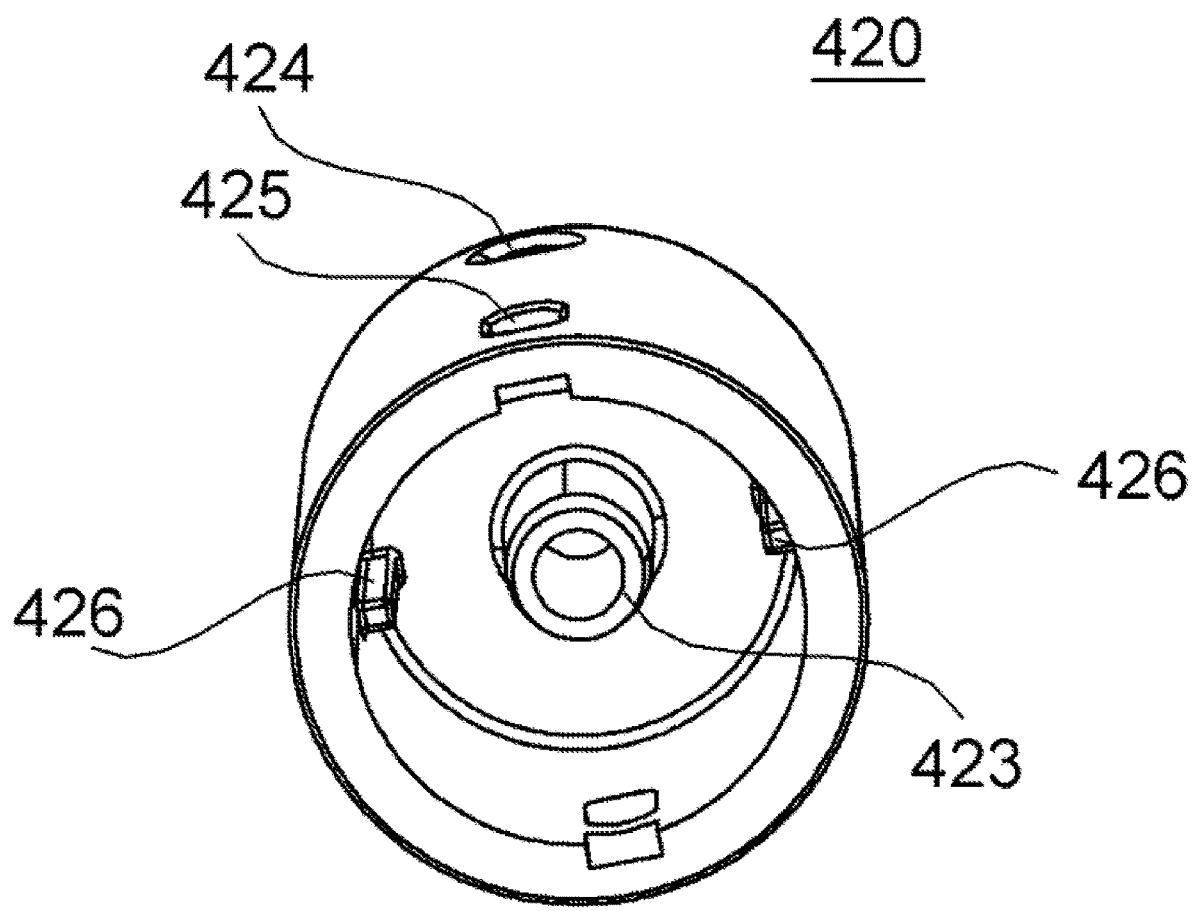
FIG. 9 is a bottom view illustrating the first member.

FIG. 7 is a perspective view illustrating the first member 420 shown in FIG. 3, FIG. 8 is a cross-sectional view illustrating the first member 420 taken along line A-A of FIG. 7, and FIG. 9 is a bottom view illustrating the first member 420.

Referring to FIGS. 7 to 9, the first member 420 is a member such as a push button which is pushed by the user. The first member 420 may be a cylindrical member. The first member 420 may include a top surface 421 and a side surface 422. The first member 420 may be a member with an open bottom. The top surface 421 is a part which is pushed by the user. The first member 420 may include a tube 423. The tube 423 is disposed inside the first member 420. The tube 423 may protrude downward from an inner surface of the first member 420. The tube 423 pressurizes the sealing member 410 when the first member 420 moves downward. A connection hole 424 is disposed inside the side surface 422. The connection hole 424 communicates with the tube 423. Also, a slot 425 may be disposed at the side surface 422. Meanwhile, the first member 420 may include a guide 426. The guide 426 is disposed on an inner surface of the side surface 422. The guide 426 may be disposed in a vertical direction. The slot 425 and the guide 426 are configured to slidably couple the first member 420 and the second member 430 with each other.

Figure 10:
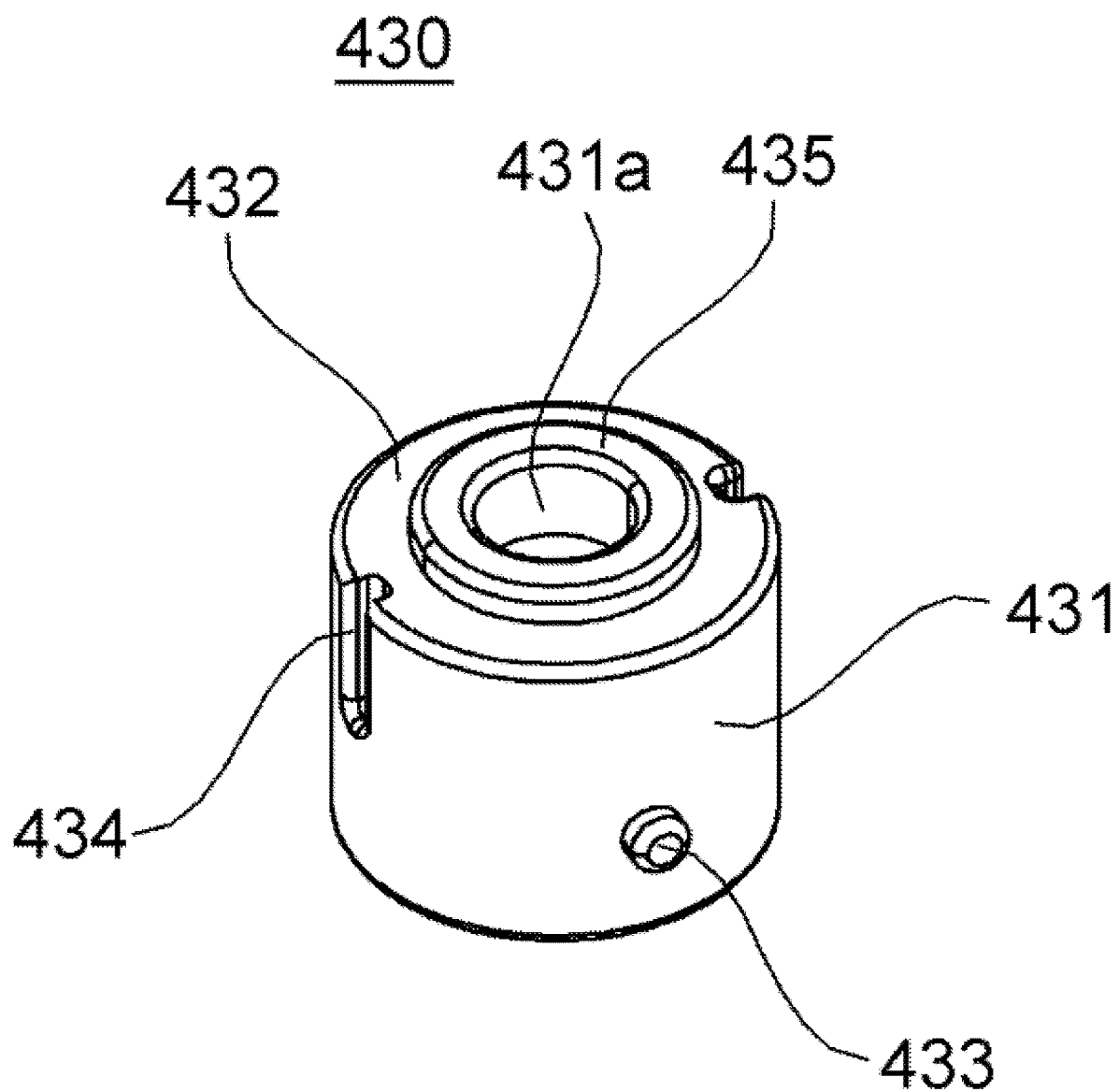
FIG. 10 is a view illustrating a second member shown in FIG. 3.

FIG. 10 is a view illustrating the second member 430 shown in FIG. 3.

Referring to FIGS. 3 and 10, the second member 430 fixes the sealing member 410 to the deaeration pipe 130. An inner surface of the second member 430 comes into contact with the sealing member 410. Also, the second member 430 guides vertical movement of the first member 420. The second member 430 may be a cylindrical member. The second member 430 may include a top surface 432 and a side surface 431. The second member 430 may be a member with an open bottom. A through hole 431a may be disposed at a center of the second member 430. The tube 423 passes through the through hole 431a. The through hole 431a is aligned with the incised portion 412 of the sealing member 410. The tube 423 passes through the through hole 431a and comes into contact with the incised portion 412. A protrusion 433 may be disposed on the side surface 431. The second member 430 is disposed inside the first member 420, and the protrusion 433 is disposed in the slot 425. When the protrusion 433 is held by a sidewall of the slot 425, vertical movement of the first member 420 is restricted. Meanwhile, a guide groove 434 may be disposed at the side surface 431. The second member 430 is disposed inside the first member 420, and the guide 426 is disposed in the guide groove 434. The guide groove 434 guides the vertical movement of the first member 420. A boss portion 435 may protrude from the top surface 432 of the second member 430. The boss portion 435 is configured to guide the elastic member 440.

Referring to FIG. 2, the elastic member 440 may be disposed between the first member 420 and the second member 430 in a vertical direction. The elastic member 440 may be a member having a restoring force when being compressed. For example, the elastic member 440 may be a compression coil spring.

Referring to FIG. 2, when an external force is not present, the hole 140 is closed by the sealing member 410. The first member 420 is spaced apart from the second member 430 until being held by a bottom end of the slot 425 due to the restoring force of the elastic member 440. Here, the tube 423 does not pressurize the sealing member 410.

Figure 11:
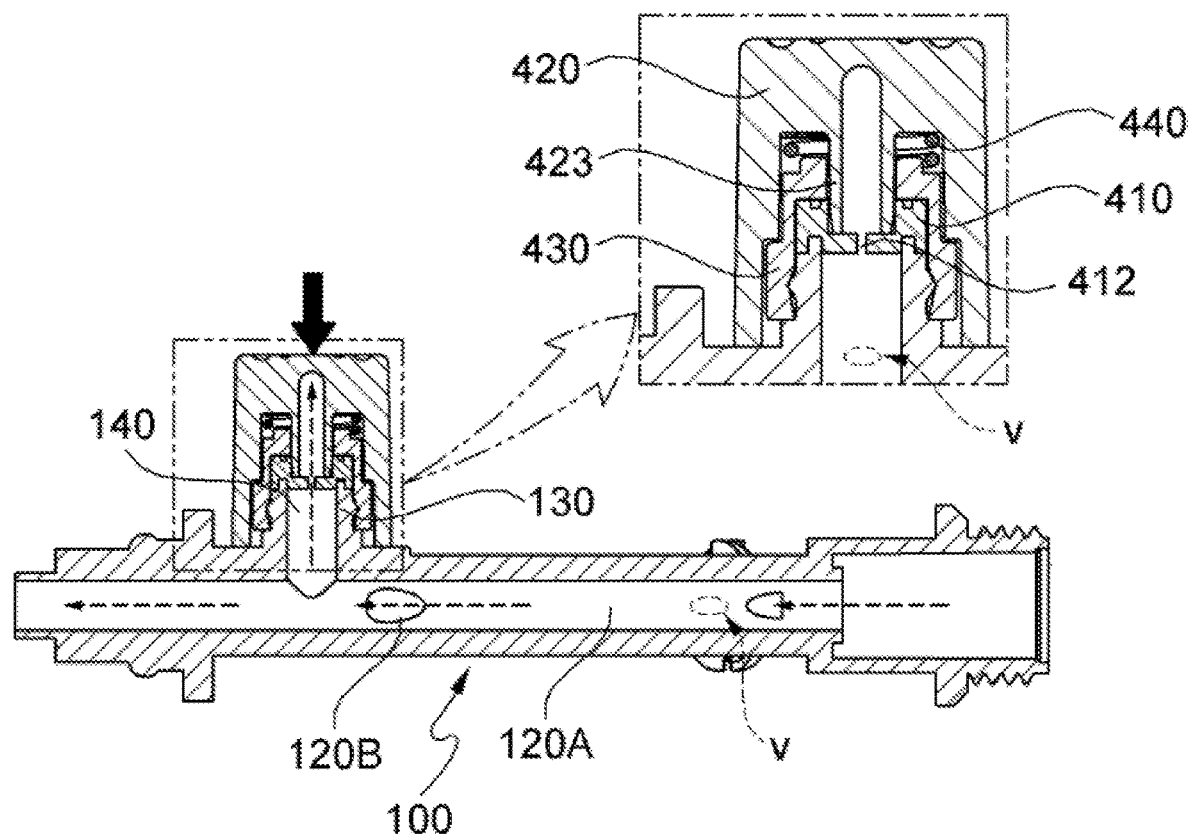
FIG. 11 is a side cross-sectional view illustrating the connector and the opening and closing portion in which a flow of bubbles is shown.
Figure 12:
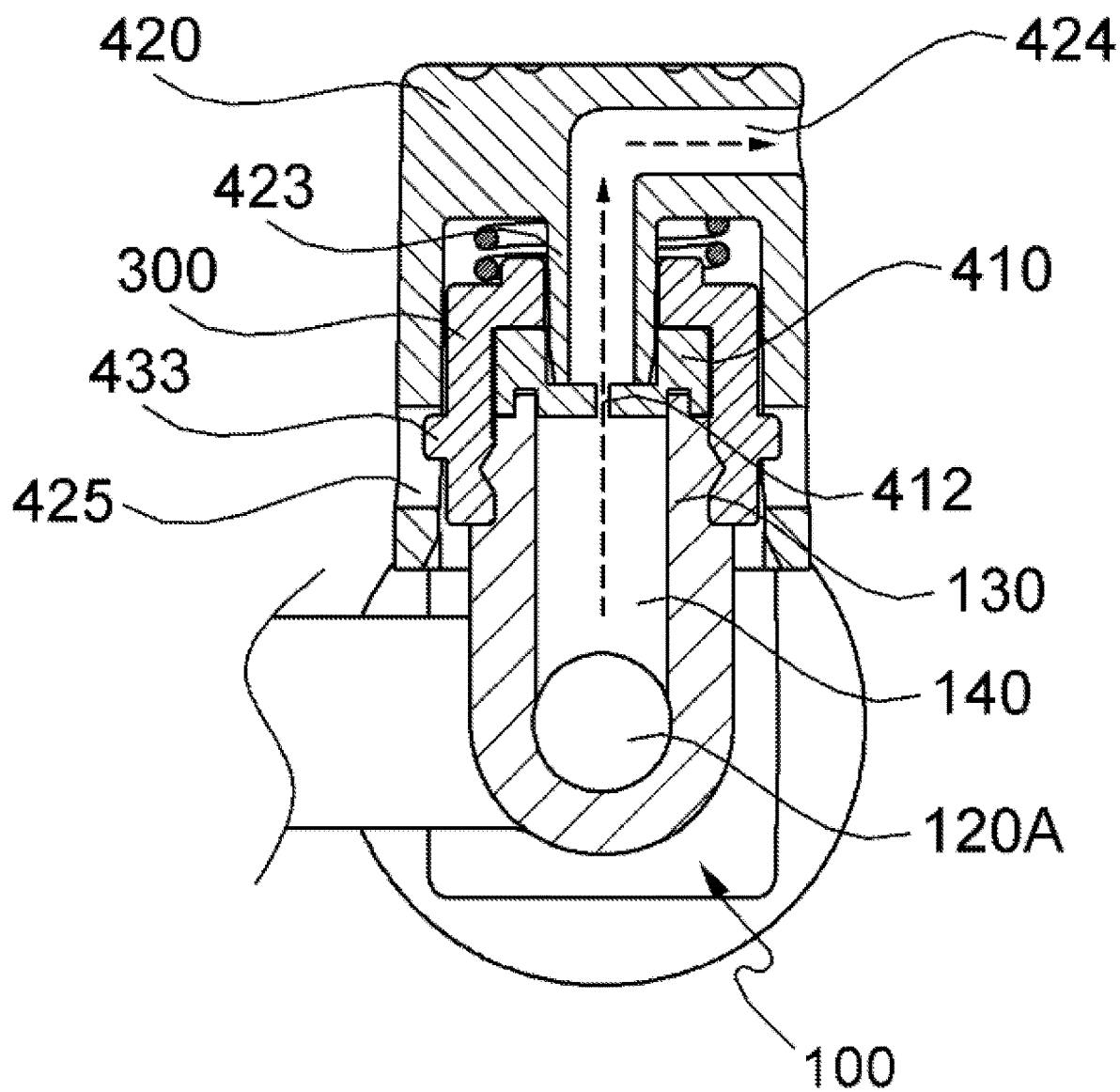
FIG. 12 is a front cross-sectional view illustrating the connector and the opening and closing portion in which the flow of bubbles is shown.

FIG. 11 is a side cross-sectional view illustrating the connector 100 and the opening and closing portion 400 in which a flow of bubbles is shown, and FIG. 12 is a front cross-sectional view illustrating the connector 100 and the opening and closing portion 400 in which the flow of bubbles is shown.

Referring to FIGS. 11 and 12, when bubbles in the channel 120 are seen during treatment, the user pushes the first member 420. When the first member 420 is pushed, the tube 423 pressurizes the incised portion 412 while moving downward. Then, as the sealing member 410 is deformed, the incised portion 412 extends and the hole 140 communicates with the tube 423. The tube 423 communicates with the outside through the connection hole 140 so as to be in an atmospheric pressure state. When the hole 140 communicates with the tube 423, a pressure of the channel 120 is higher than a pressure of the tube 423 such that bubbles v existing in the channel 120 flow into the hole 140. The bubbles v flowing into the hole 140 pass through the tube 423 and a connection hole 424 and are discharged outward. When the user takes a user's hand off from the first member 420, the first member 420 moves upward due to the restoring force of the elastic member 440. When the first member 420 moves upward, the tube 423 moves upward such that the sealing member 410 is released from being pressurized. When being pressurized is released, a shape of the sealing member 410 is restored such that the incised portion 412 contracts and the hole 140 is closed again.

A part pushed by the user is the top surface 421 (refer to FIG. 7) of the first member 420. Also, a part where the connection hole 424 is disposed is the side surface 422 of the first member 420. Accordingly, since a contact area between the user's hand, in detail, a user's finger and the first member 420 is distinctly distinguished from a discharge area of the bubbles v not to interfere with each other, the bubbles v may be more easily discharged.

When the embodiment is used, the user may remove the bubbles v using a simple operation during a process of inserting the catheters 10 into blood vessels. Also, since the bubbles v are removed using a pressure difference between inside and outside the connector 100, it is possible to effectively prevent the bubbles v from flowing into blood vessels. The above-described method enhances a success rate of treatment. Also, an advantage of significantly reducing a fatigue level of the user during a treatment process is present.

Also, when the user sees the bubbles v even while pushing the catheters 10, the bubbles v may be removed using a simple operation of pushing the opening and closing portion 400 such that additional treatment of removing the bubbles v is not necessary. Also, since the user may remove the bubbles v single-handed, an assistant staff for removing the bubbles v is unnecessary. Also, it is possible to expedite treatment.

Also, since an operation of removing the bubbles v is easily repeated, it is possible to effectively prevent the bubbles v from flowing into blood vessels. Also, since it is possible to decrease a skill level required by a practitioner, it is easy to secure practitioners.

As an example, the opening and closing portion 400 may be operated by a turning operation of the user.

Figure 13:
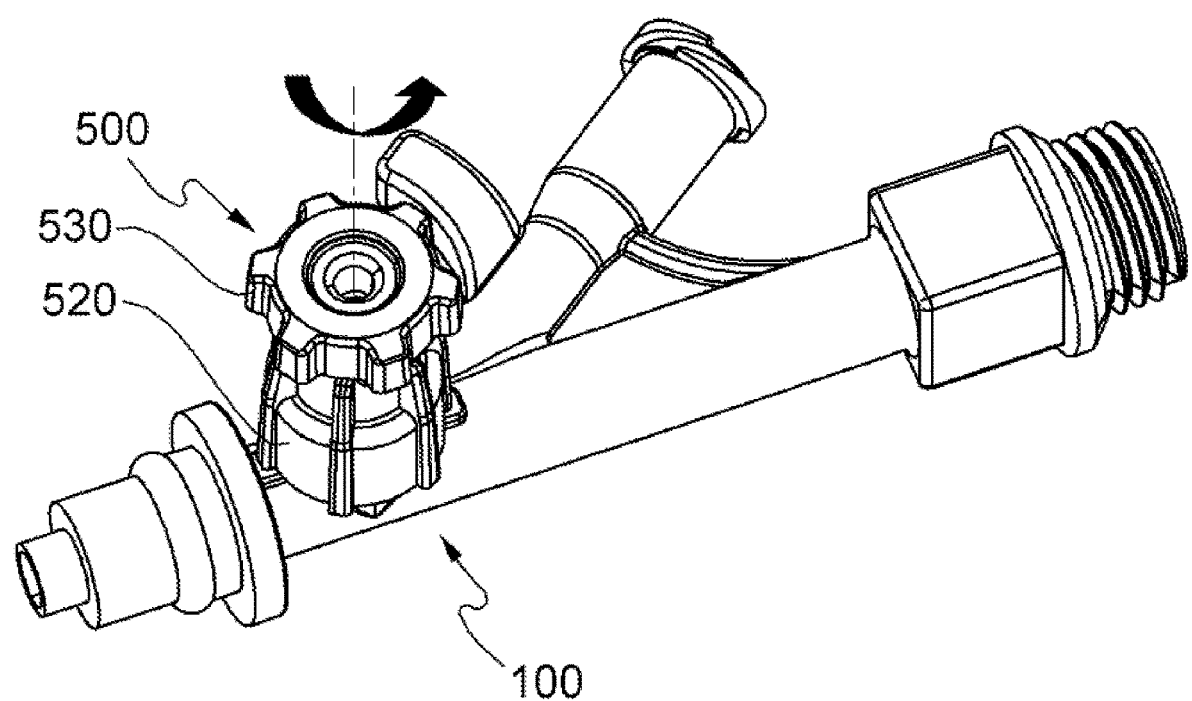
FIG. 13 is a view illustrating a modified example of the opening and closing portion.
Figure 14:
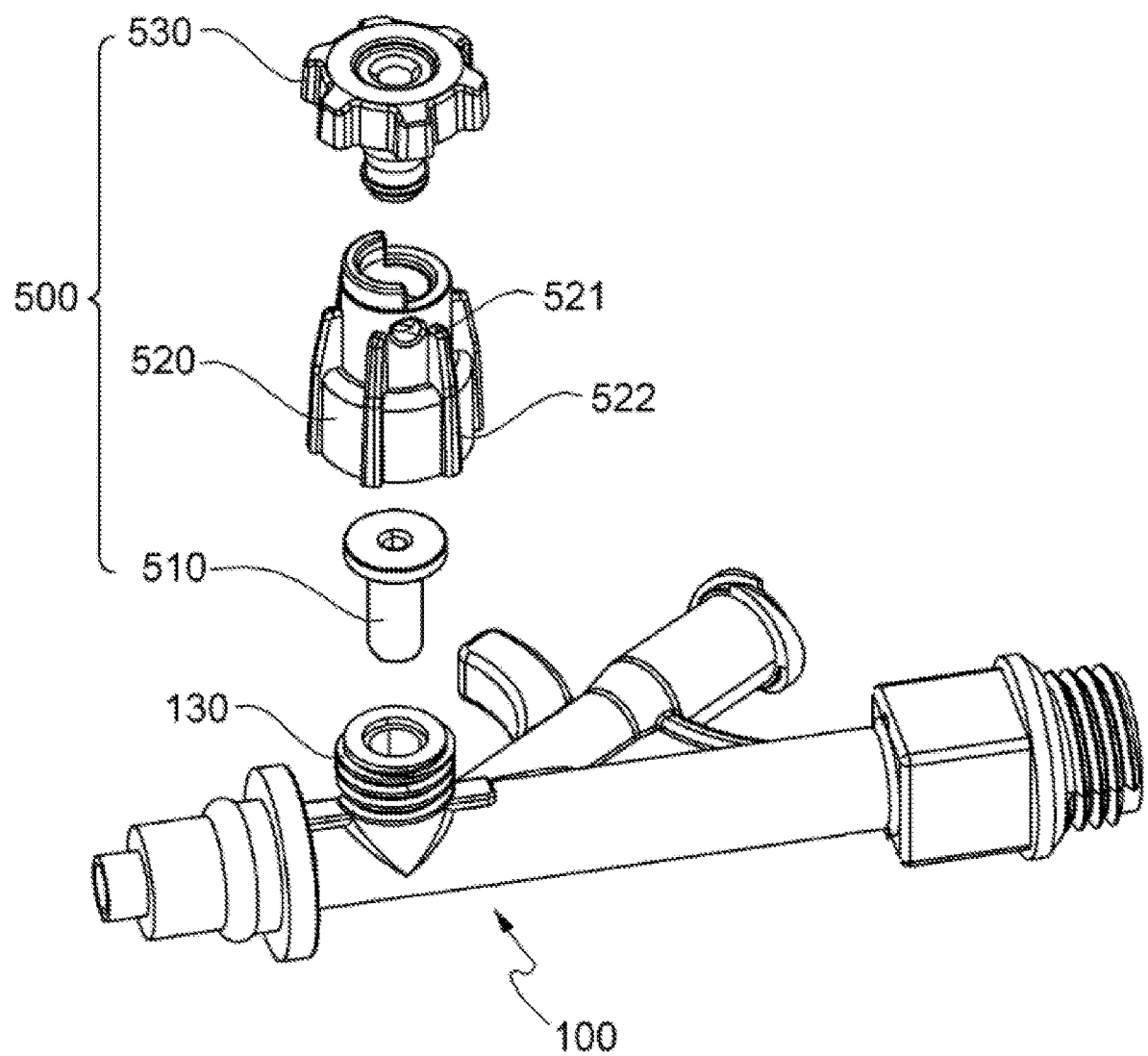
FIG. 14 is an exploded view illustrating the opening and closing portion shown in FIG. 13.

FIG. 13 is a view illustrating a modified example of the opening and closing portion, and FIG. 14 is an exploded view illustrating an opening and closing portion 500 shown in FIG. 13.

As an example, the opening and closing portion 500 may be operated by a turning operation of the user.

Referring to FIGS. 13 and 14, the opening and closing portion 500 may include a sealing member 510, a first member 520, and a second member 530. The sealing member 510 may be disposed at the deaeration pipe 130. The first member 520 may be rotationally fastened to the deaeration pipe 130. The second member 530 may be rotationally coupled with the first member 520.

Figure 15:
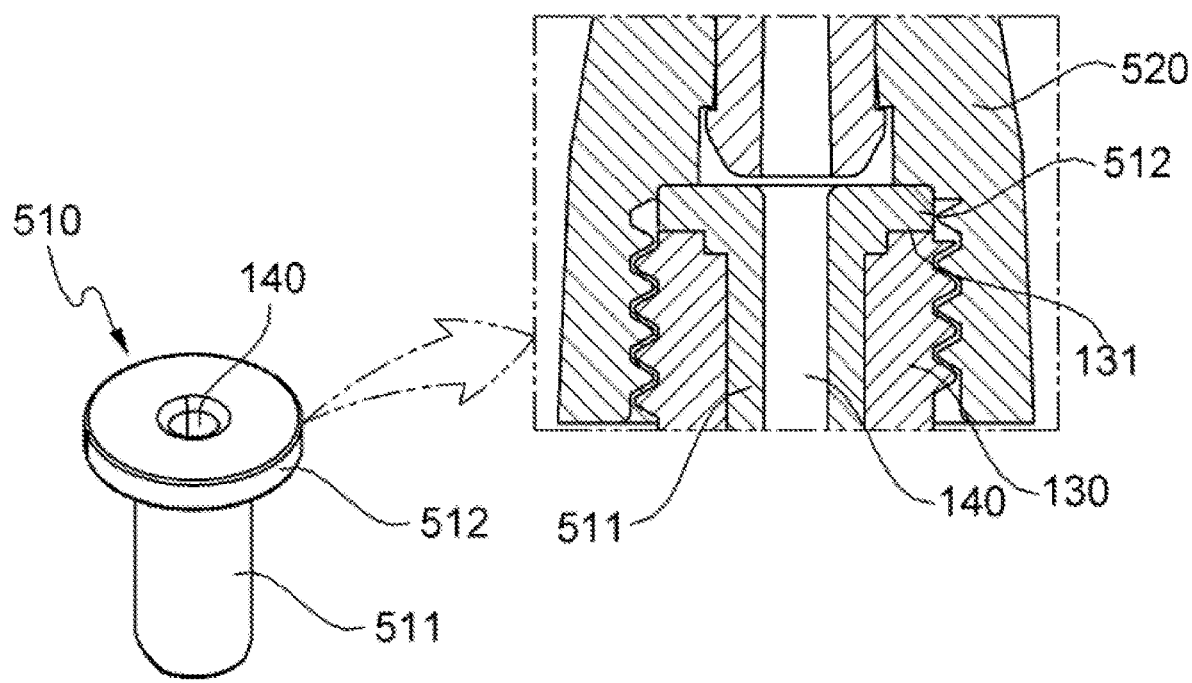
FIG. 15 is a side cross-sectional view illustrating the opening and closing portion shown in FIG. 13.
Figure 16:
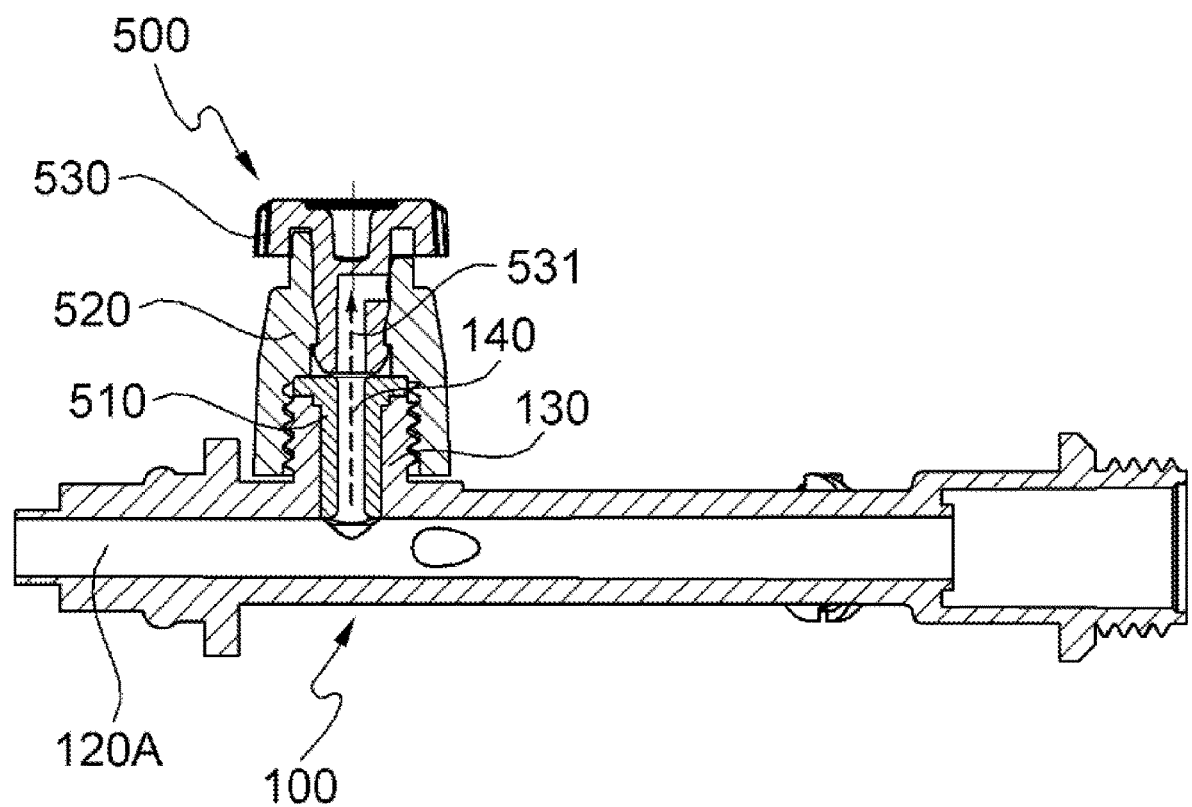
FIG. 16 is a perspective view illustrating a sealing member.
Figure 17:
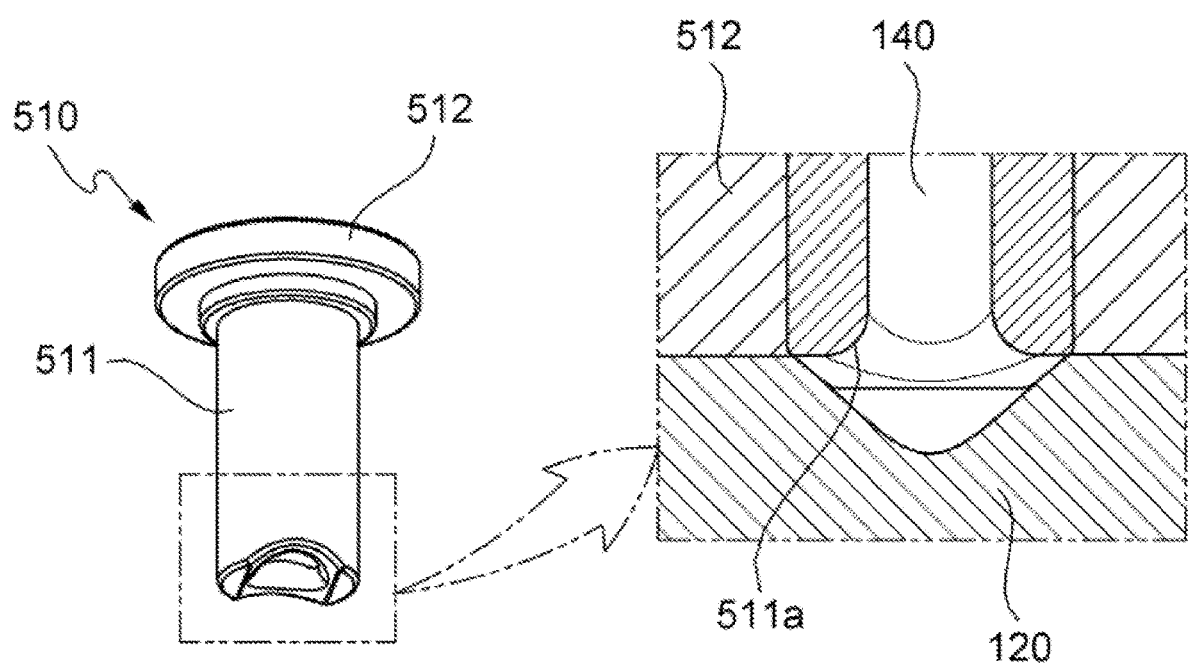
FIG. 17 is a side view illustrating the sealing member.

FIG. 15 is a side cross-sectional view illustrating the opening and closing portion 500 shown in FIG. 13, FIG. 16 is a perspective view illustrating the sealing member 510, and FIG. 17 is a side view illustrating the sealing member 510.

Referring to FIGS. 14 to 17, the sealing member 510 seals a space between the first member 520 and the deaeration pipe 130. The sealing member 510 may be a cylindrical member. The sealing member 510 may include a first part 511 and a second part 512. An outer diameter of the second part 512 may be greater than an outer diameter of the first part 511. The first part 511 is disposed inside the deaeration pipe 130. The second part 512 may be disposed to cover a top surface 131 of the deaeration pipe 130. The second part 512 is disposed outside the deaeration pipe 130. A bottom surface of the second part 512 may come into contact with the top surface 131 of the deaeration pipe 130. A top surface of the second part 512 may come into contact with an inner surface of the first part 520. The hole 140 is disposed at a center of the sealing member 510. The hole 140 communicates with the channel 120. The hole 140 is disposed while passing through a top end and a bottom end of the sealing member 510. A boundary between a bottom surface of the first part 511 and the hole 140 may be formed as a curved surface 511a (refer to FIG. 16). The curved surface 511a induces the bubbles v of the channel 120 to more easily flow in toward the hole 140.

The first member 520 may be rotationally fastened to the deaeration pipe 130. A screw thread may be formed on the inner surface of the first member 520. A screw thread may be formed outside the deaeration pipe 130 corresponding to the screw thread of the first member 520. The first member 520 may include a plurality of ribs 522 protruding from an outer surface thereof. The ribs 522 may allow products to be easily assembled in production. The first member 520 may include a discharge hole 521. The discharge hole 521 may allow inside and outside of the first member 520 to communicate with each other.

The second member 530 is rotationally coupled with the first member 520. A top of the second member 530 is formed as a knob. A bottom of the second member 530 may be disposed inside the first member 520. A connection hole 531 is disposed below the second member 530. The connection hole 531 communicates with the hole 140 of the sealing member 510. According to rotation of the second member 530, the connection hole 531 and the discharge hole 521 are aligned to communicate with each other or are misaligned from each other such that the connection hole 531 is blocked by the first member 520.

Figure 18:
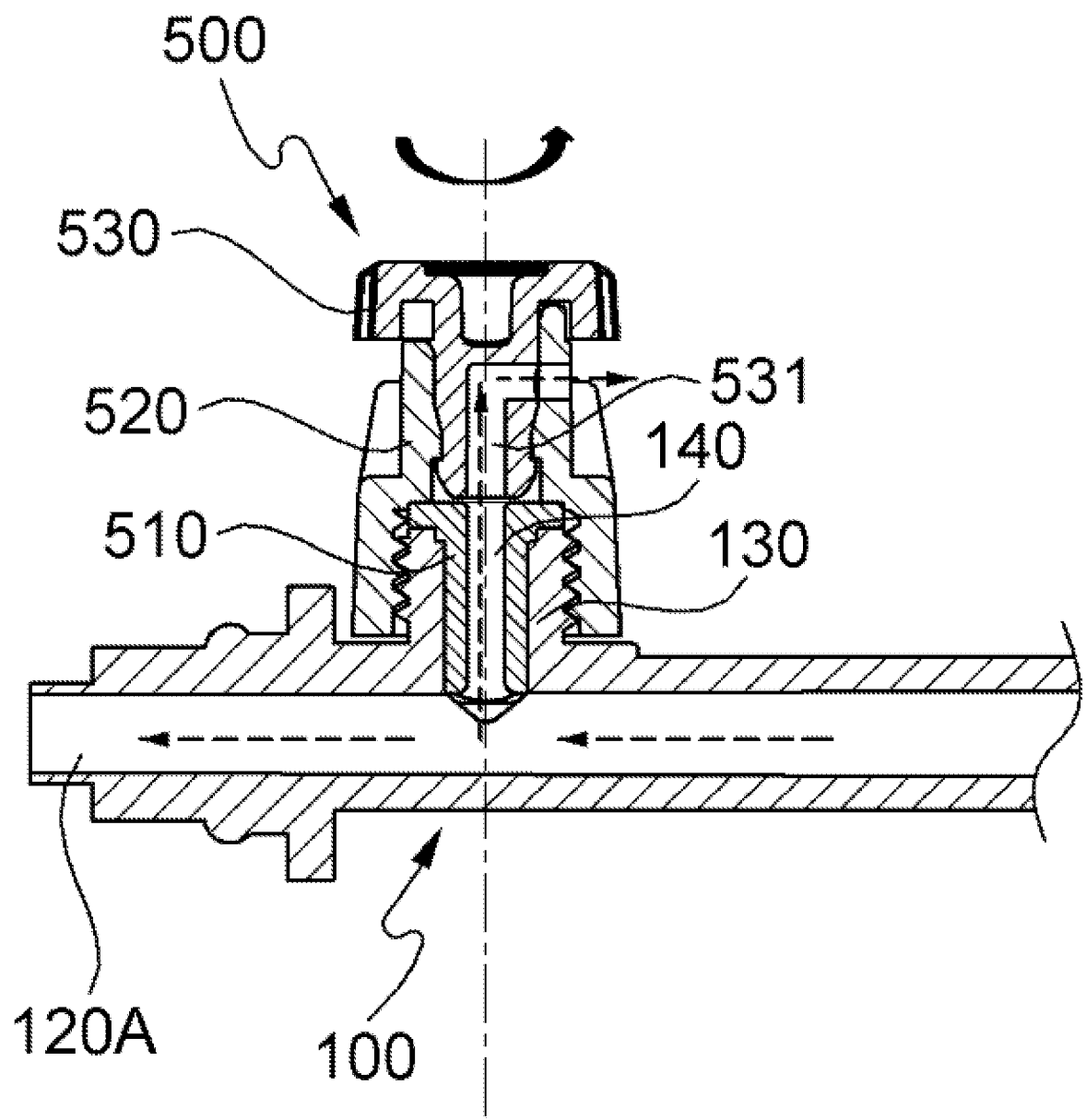
FIG. 18 is a view illustrating a state in which the hole is opened by the opening and closing portion of FIG. 13.

FIG. 18 is a view illustrating a state in which the hole 140 is opened by the opening and closing portion 500 of FIG. 13.

Referring to FIG. 13, when the bubbles v in the channel 120 are seen during treatment, the user turns the second member 530. When the second member 530 is turned until being not further turned, the connection hole 531 and the discharge hole 521 are aligned. When the connection hole 531 and the discharge hole 521 are aligned with each other, a pressure of the channel 120 is higher than a pressure of the connection hole 531 such that the bubbles v existing in the channel 120 flow into the hole 140. The bubbles v flowing into the hole 140 pass through the connection hole 531 and the discharge hole 521 and are discharged outward.

Figure 19:
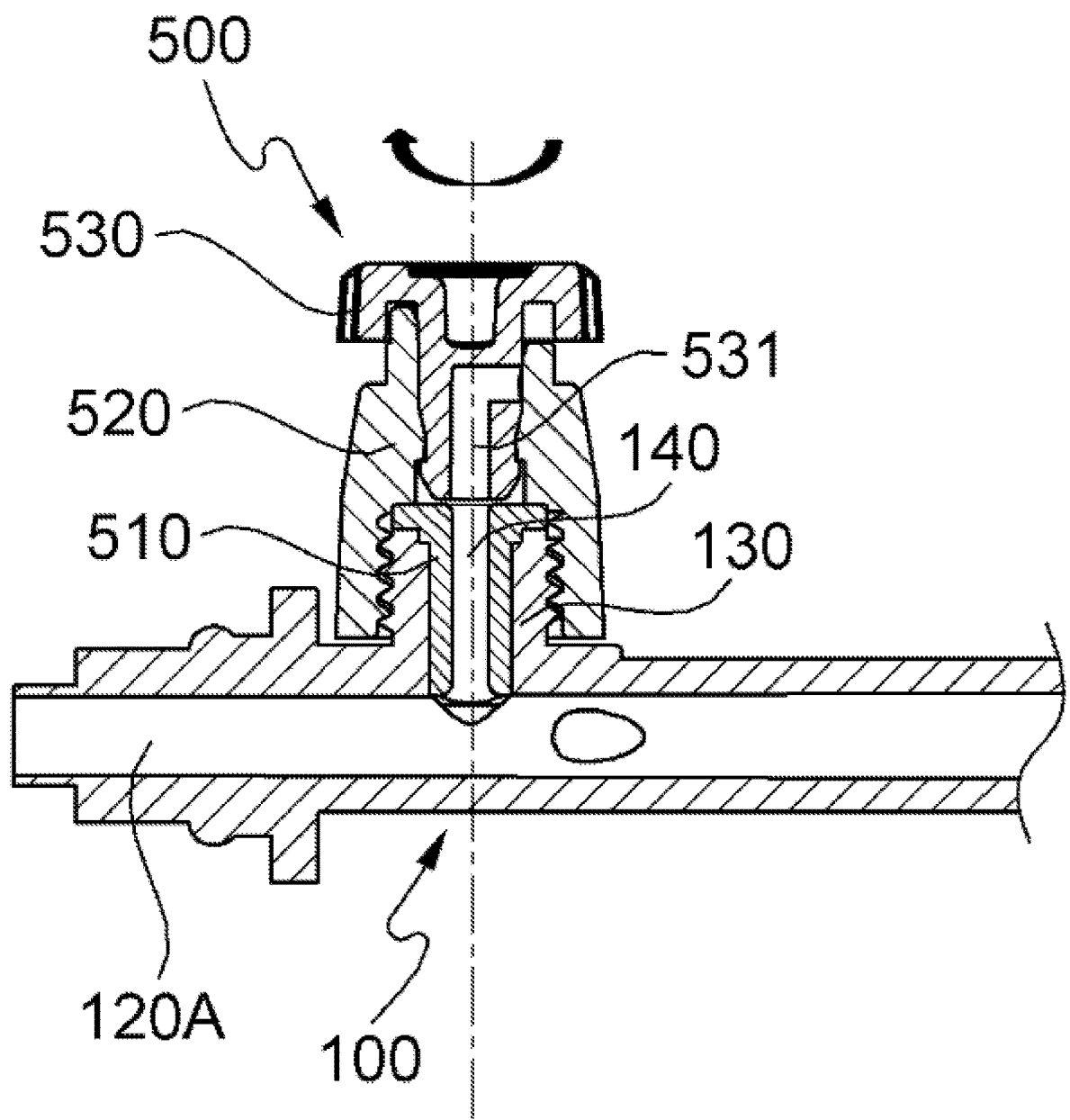
FIG. 19 is a view illustrating a state in which the hole is closed by the opening and closing portion of FIG. 13.

FIG. 19 is a view illustrating a state in which the hole 140 is closed by the opening and closing portion 500 of FIG. 13.

Referring to FIG. 19, when the user reversely turn the second member 530, the connection hole 531 and the discharge hole 521 are misaligned from each other such that the connection hole 531 is closed. When the connection hole 531 is closed, the hole 140 is closed.

A turning operation with respect to the second member 530 is a very simple operation performable by a practitioner single-handed. Also, repetitiveness and easiness thereof are high such that it is possible to immediately remove bubbles during treatment.

Figure 20:
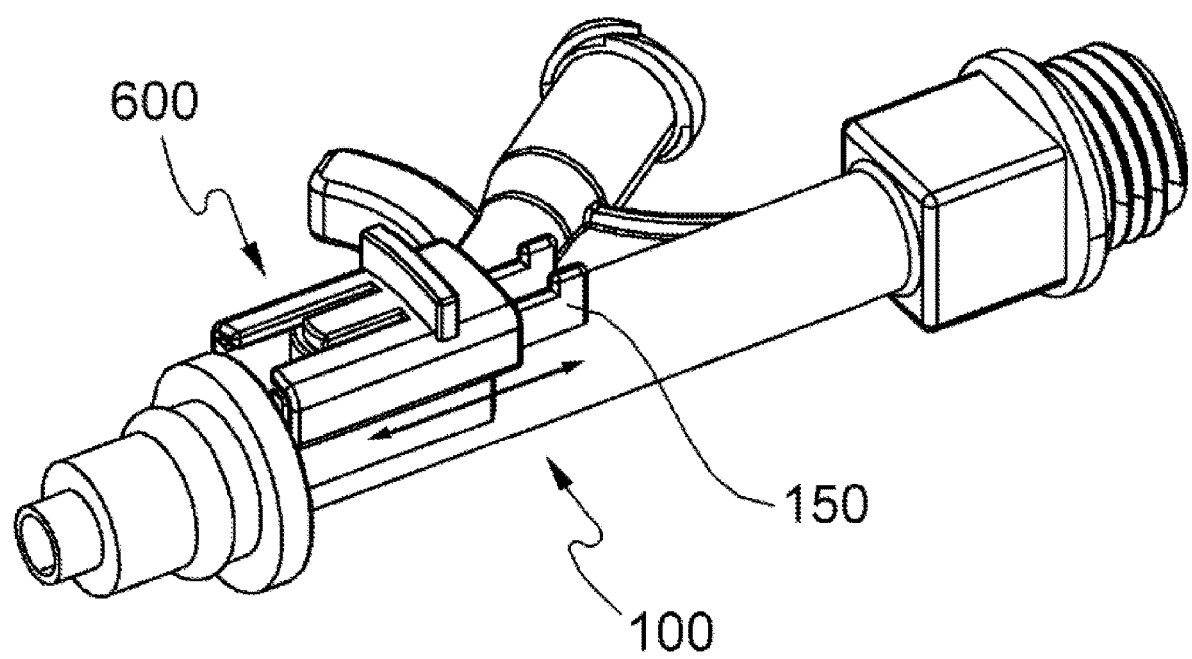
FIG. 20 is a view illustrating another modified example of the opening and closing portion.
Figure 21:
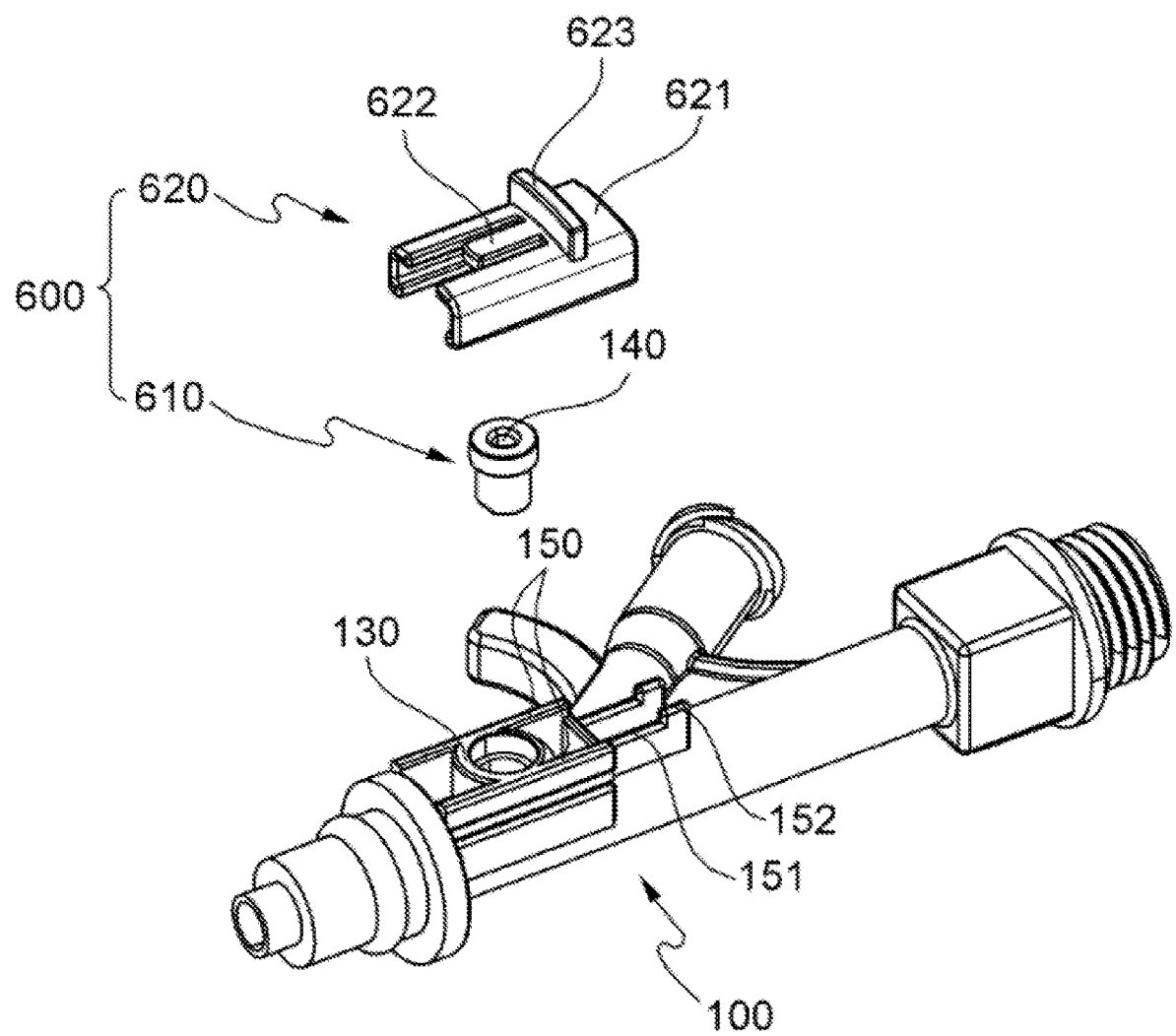
FIG. 21 is an exploded view illustrating the opening and closing portion shown in FIG. 20.
Figure 22:
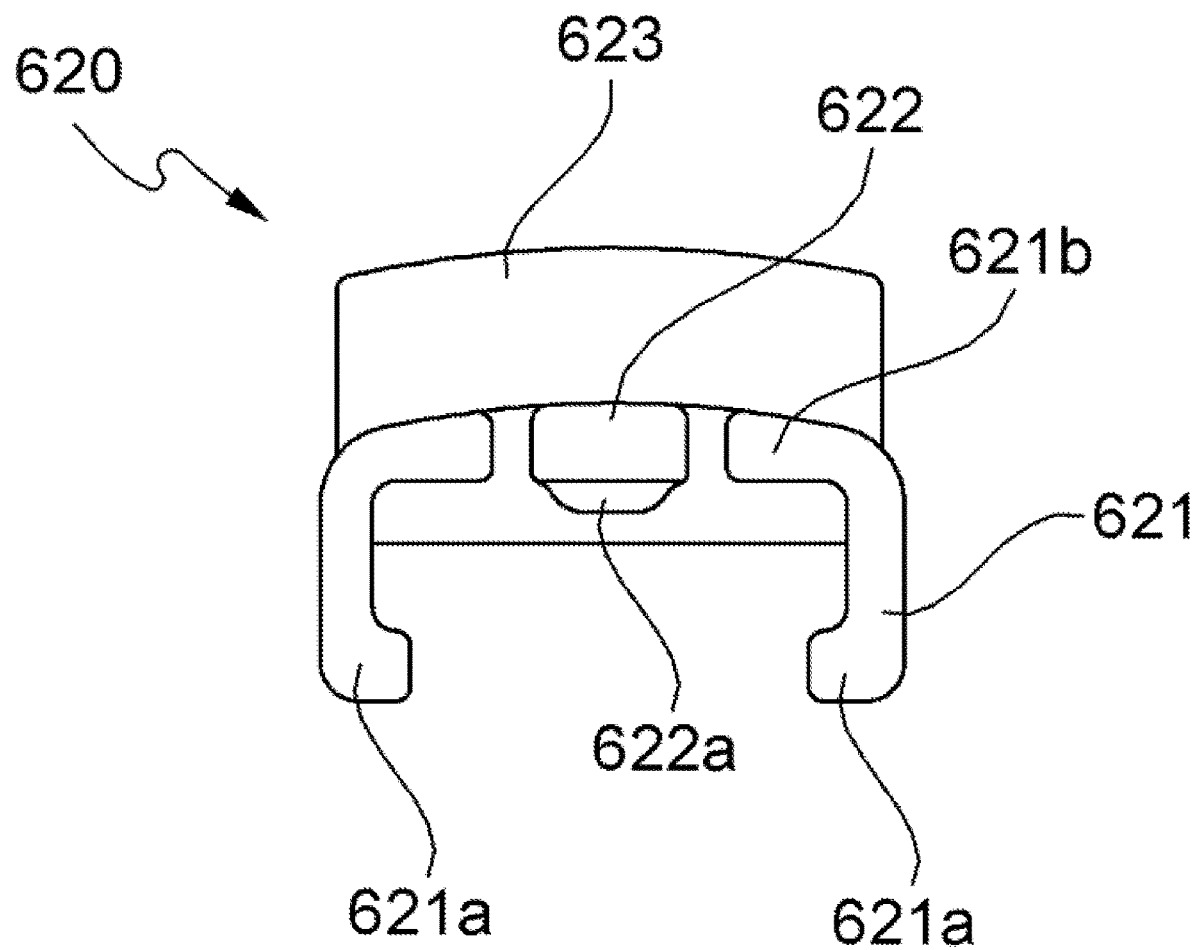
FIG. 22 is a front view illustrating a first member shown in FIG. 21.

FIG. 20 is a view illustrating another modified example of the opening and closing portion, FIG. 21 is an exploded view illustrating an opening and closing portion 600 shown in FIG. 20, and FIG. 22 is a front view illustrating a first member 620 shown in FIG. 21.

As an example, the opening and closing portion 600 may be operated by a push-and-pull operation of the user.

Referring to FIGS. 20 and 21, the opening and closing portion 600 may include a sealing member 610 and a first member 620. The sealing member 610 may be disposed at the deaeration pipe 130. The hole 140 is disposed at a center of the sealing member 610. The hole 140 communicates with the channel 120. The first member 620 may be slidably coupled to the connector 100. The connector 100 may include a pair of guides 150. The guides 150 may protrude from a surface of the connector 100. The pair of guides 150 may be disposed with the deaeration pipe 130 therebetween. The first member 620 linearly moves along the guides 150. As the first member 620 moves, the hole 140 disposed in the sealing member 610 is selectively opened or closed.

Referring to FIGS. 20 to 22, the first member 620 may include a body 621 and a cover 622. The body 621 and the cover 622 are merely described while being distinguished according to functions and shapes but may be one member. The body 621 may be slidably coupled with the guides 150. The cover 622 may be disposed at the body 621 in an elastically deformable cantilever form. A first protrusion 622a protrudes from a bottom surface of the cover 622. The first protrusion 622a covers the hole 140 of the sealing member 610. Rails 621a may be disposed at a bottom end of a side surface of the body 621. The rails 621a may come into contact with grooves or protrusions disposed on the guides 150 and guide movement of the first member 620. Second protrusions 621b are disposed at a rear end of the body 621. The second protrusions 621b are held by stoppers 152.

The guides 150 may include the stoppers 152. The stoppers 152 restrict movement of the first member 620. The stoppers 152 may be protrusions protruding upward from extending portions 151 of the guides 150.

A rib 623 may protrude from a top end of the body 621. The rib 623 allows the user to easily perform a push or pull operation.

Figure 23:
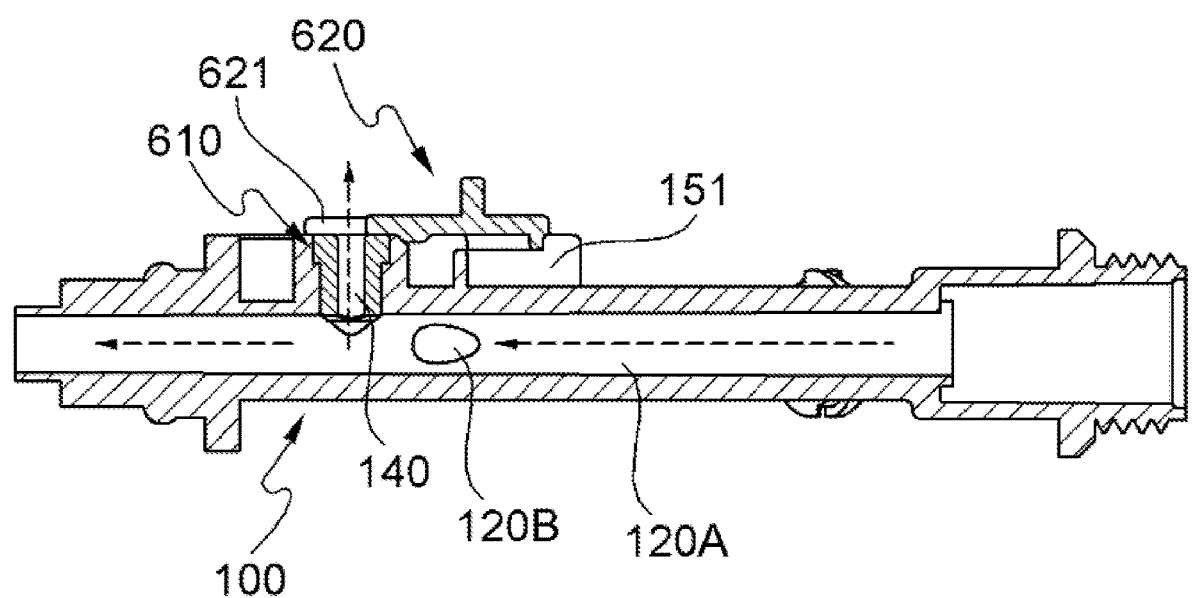
FIG. 23 is a side cross-sectional view illustrating the opening and closing portion of FIG. 20 and the connector.
Figure 24A:
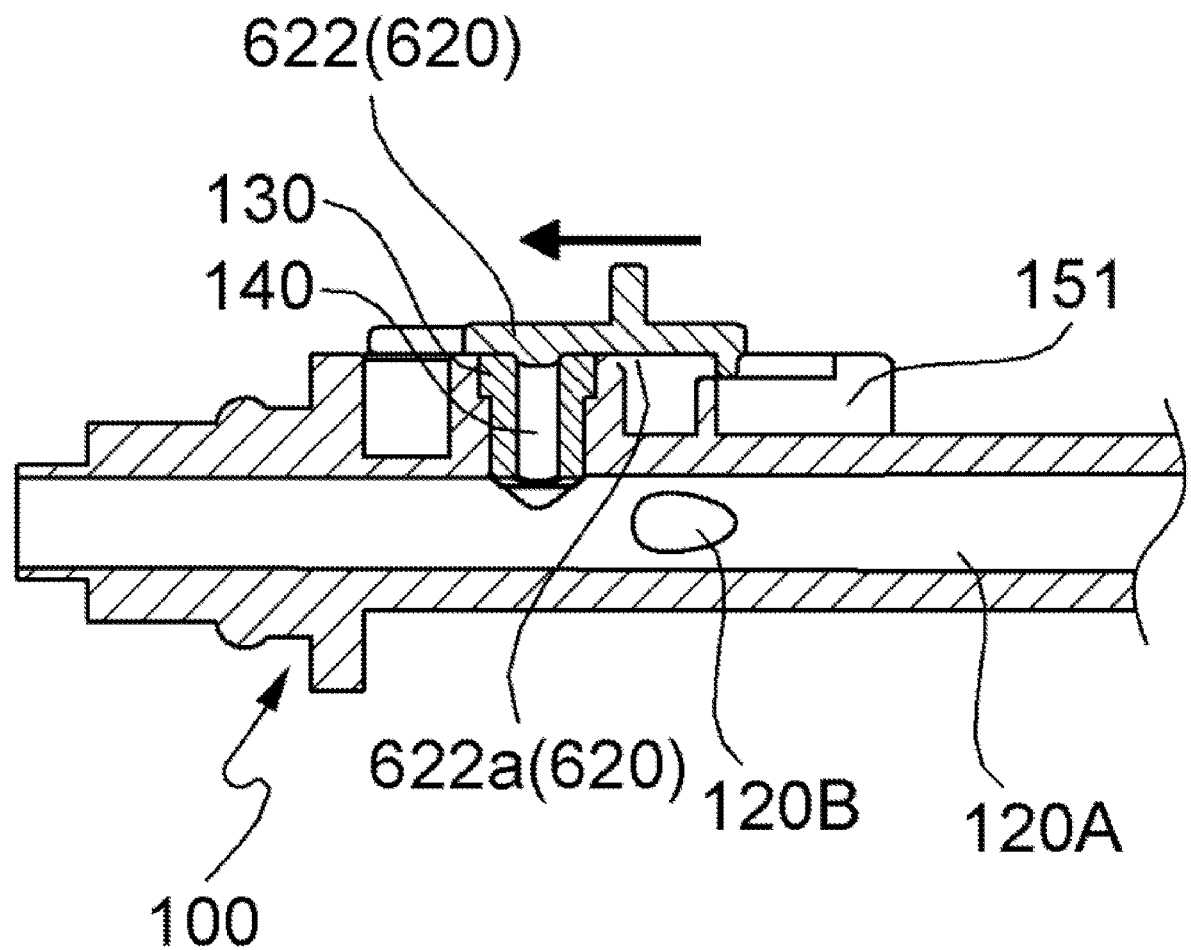
FIGS. 24A and 24B are views illustrating states in which the hole is opened and closed by the opening and closing portion of FIG. 20.
Figure 24B:
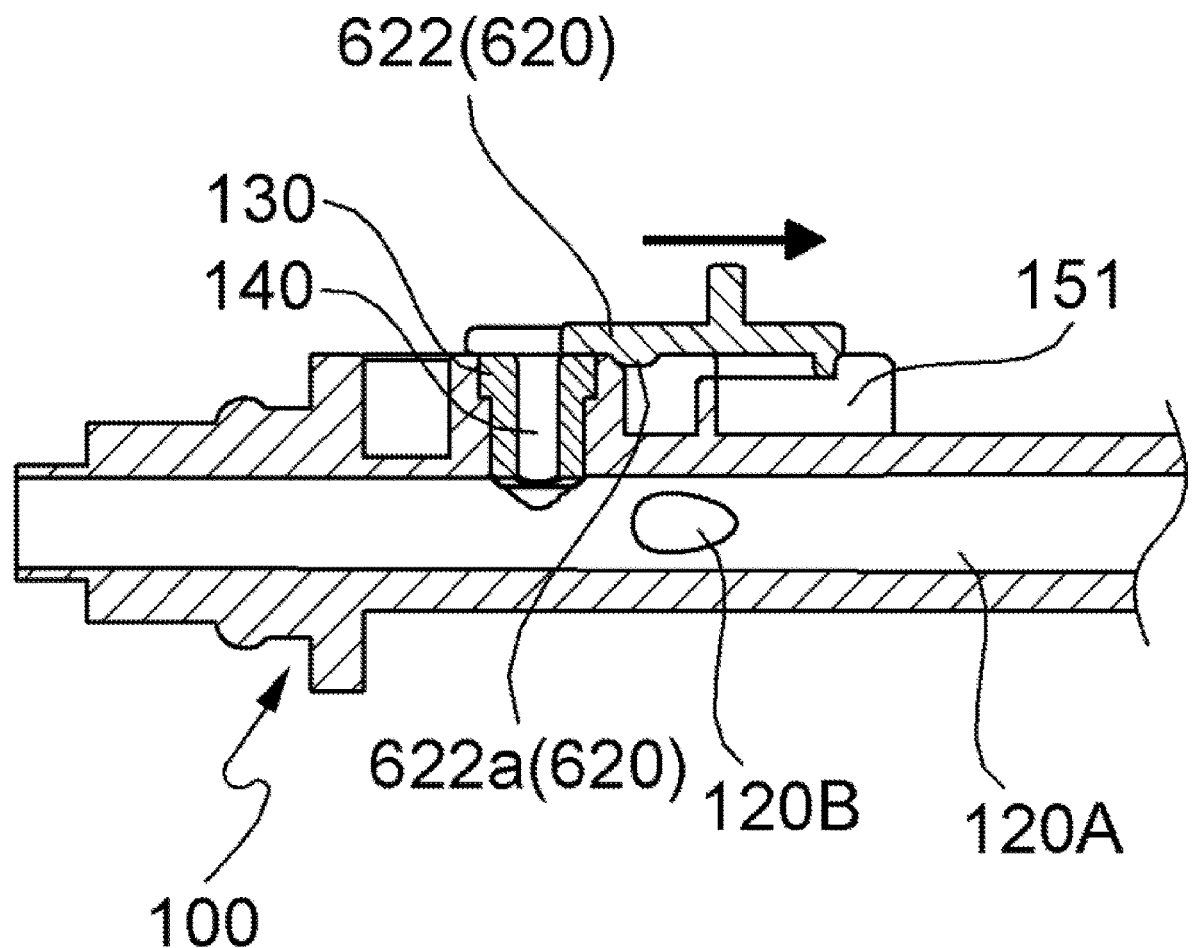

FIG. 23 is a side cross-sectional view illustrating the opening and closing portion 600 and the connector 100, and FIGS. 24A and 24B are views illustrating states in which the hole 140 is opened and closed by the opening and closing portion 600 of FIG. 20.

Referring to FIGS. 23 and 24A, the cover 622 covers the hole 140 in a state in which the first member 620 has moved forward. Also, the first protrusion 622a is inserted into the hole 140. The first protrusion 622a blocks the hole 140 and maintains a sealed state of the channel 120. Referring to FIGS. 23 and 24B, when the bubbles v in the channel 120 are seen during treatment, the user pulls the first member 620. When the first member 620 is pulled, the cover 622 moves and the first protrusion 622a is separated from the hole 140 such that the hole 140 is opened. When the hole 140 is opened, the pressure of the channel 120 is higher than atmospheric pressure such that bubbles v existing in the channel 120 flow into the hole 140. The bubbles v flowing into the hole 140 are directly discharged outward.

Figure 25:
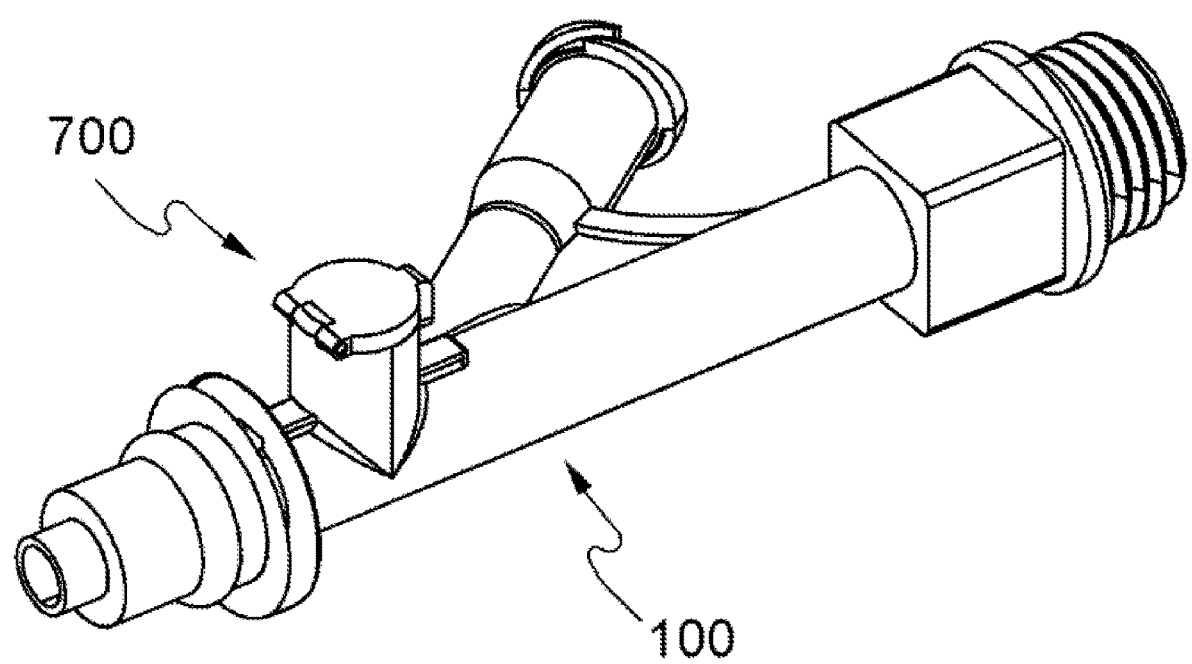
FIG. 25 is a view illustrating still another modified example of the opening and closing portion.
Figure 26:
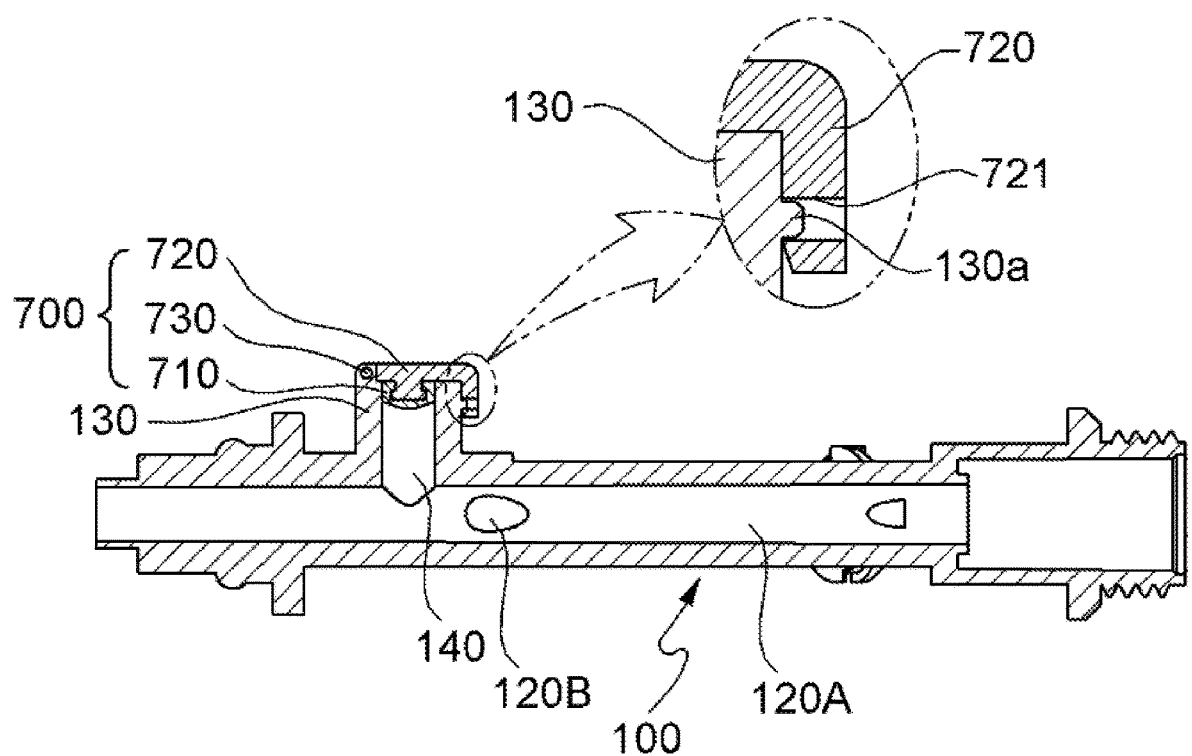
FIG. 26 is a side cross-sectional view illustrating the opening and closing portion shown in FIG. 25.

FIG. 25 is a view illustrating still another modified example of the opening and closing portion. FIG. 26 is a side cross-sectional view illustrating an opening and closing portion 700 shown in FIG. 25.

As an example, the opening and closing portion 700 may be operated by an opening operation of the user.

Referring to FIGS. 25 and 26, the opening and closing portion 700 may include a sealing member 710 and a first member 720. The sealing member 710 is disposed on the first member 720. The first member 720 may be pivotably coupled to the deaeration pipe 130. The deaeration pipe 130 includes the hole 140. The hole 140 communicates with the channel 120. The deaeration pipe 130 includes a hinge shaft 730. The first member 720 pivots on the hinge shaft 730. The first member 720 covers the hole 140. The sealing member 710 is disposed on a bottom surface of the first member 720. While the first member 720 covers the hole 140, the sealing member 710 is disposed inside the hole 140 and closes the hole 140.

The first member 720 includes a hole 721. The hole 721 may be disposed at a side surface of the first member 720. The deaeration pipe 130 may include a protrusion 130a. While the first member 720 covers the hole 140, the protrusion 130a is disposed in the hole 721.

Figure 27:
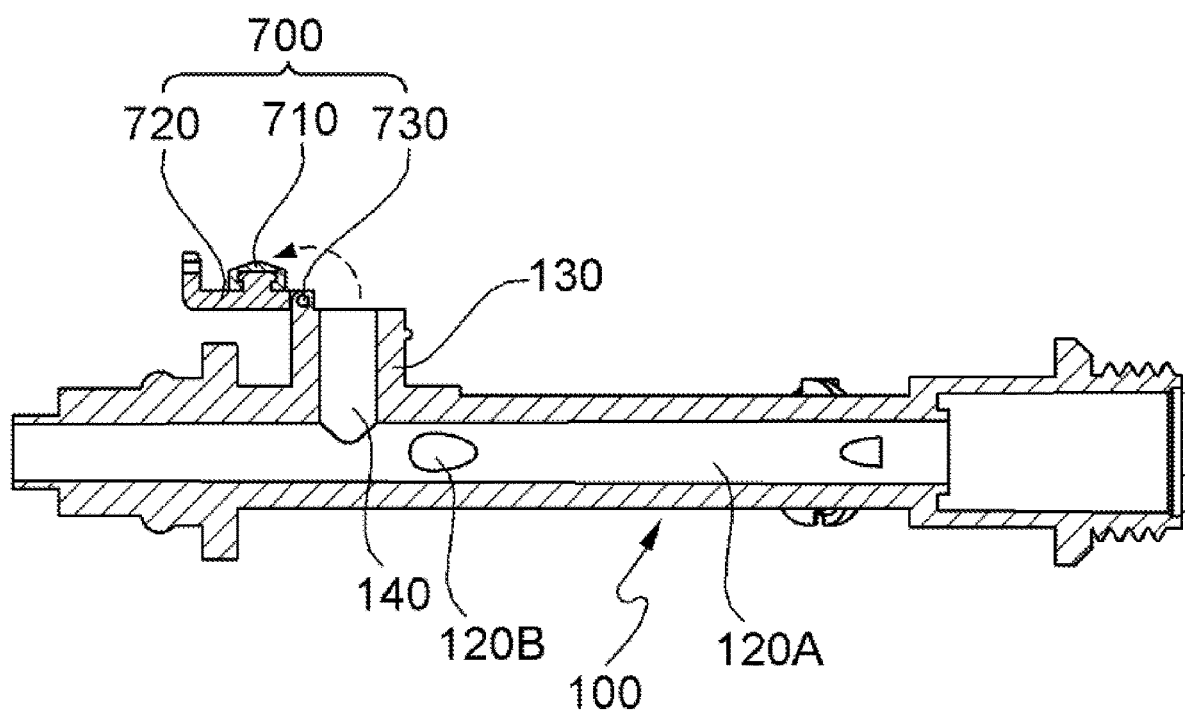
FIG. 27 is a view illustrating a state in which the hole is opened by the opening and closing portion shown in FIG. 25.

FIG. 27 is a view illustrating a state in which the hole 140 is opened by the opening and closing portion 700 shown in FIG. 25.

Referring to FIG. 27, when the bubbles v in the channel 120 are seen during treatment, the user opens the first member 720 from the deaeration pipe 130. When the first member 720 is pivoted, the sealing member 710 is separated from the hole 140 such that the hole 140 is opened. When the hole 140 is opened, the pressure of the channel 120 is higher than atmospheric pressure such that bubbles v existing in the channel 120 flow into the hole 140. The bubbles v flowing into the hole 140 are directly discharged outward.

Figure 28:
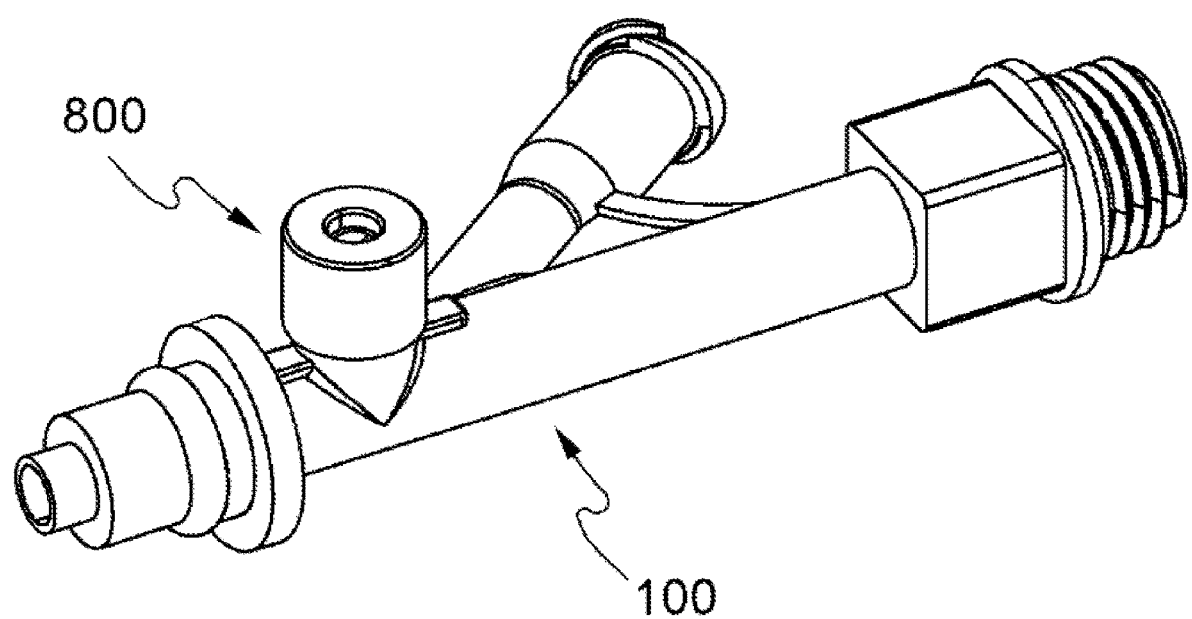
FIG. 28 is a view illustrating yet another modified example of the opening and closing portion.
Figure 29:
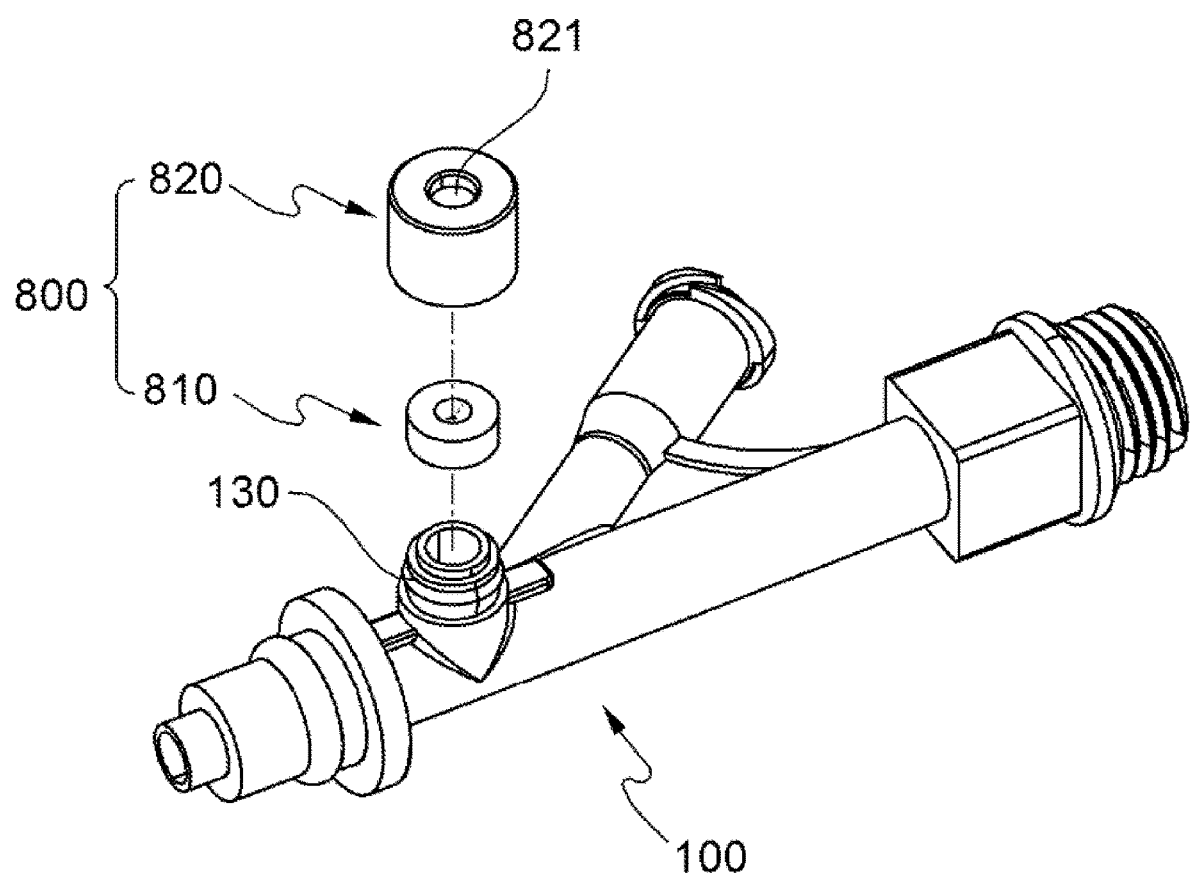
FIG. 29 is an exploded view illustrating the opening and closing portion shown in FIG. 28.

FIG. 28 is a view illustrating yet another modified example of the opening and closing portion, and FIG. 29 is an exploded view illustrating an opening and closing portion 800 shown in FIG. 28.

As an example, the opening and closing portion 800 may be operated by the user using a tool. The opening and closing portion 800 seals the hole 140, and the user may remove bubbles by injecting a simple tool such as a syringe into the opening and closing portion 800.

Referring to FIGS. 28 and 29, the opening and closing portion 800 may include a sealing member 810 and a first member 820. The sealing member 810 may be disposed at the deaeration pipe 130. The deaeration pipe 130 includes the hole 140. The hole 140 communicates with the channel 120. The sealing member 810 covers the hole 140. The first member 820 fixes the sealing member 810 to the deaeration pipe 130. The first member 820 is disposed outside the sealing member 810 and is coupled with the deaeration pipe 130. The first member 820 may be a cylindrical member with an open bottom.

Figure 30:
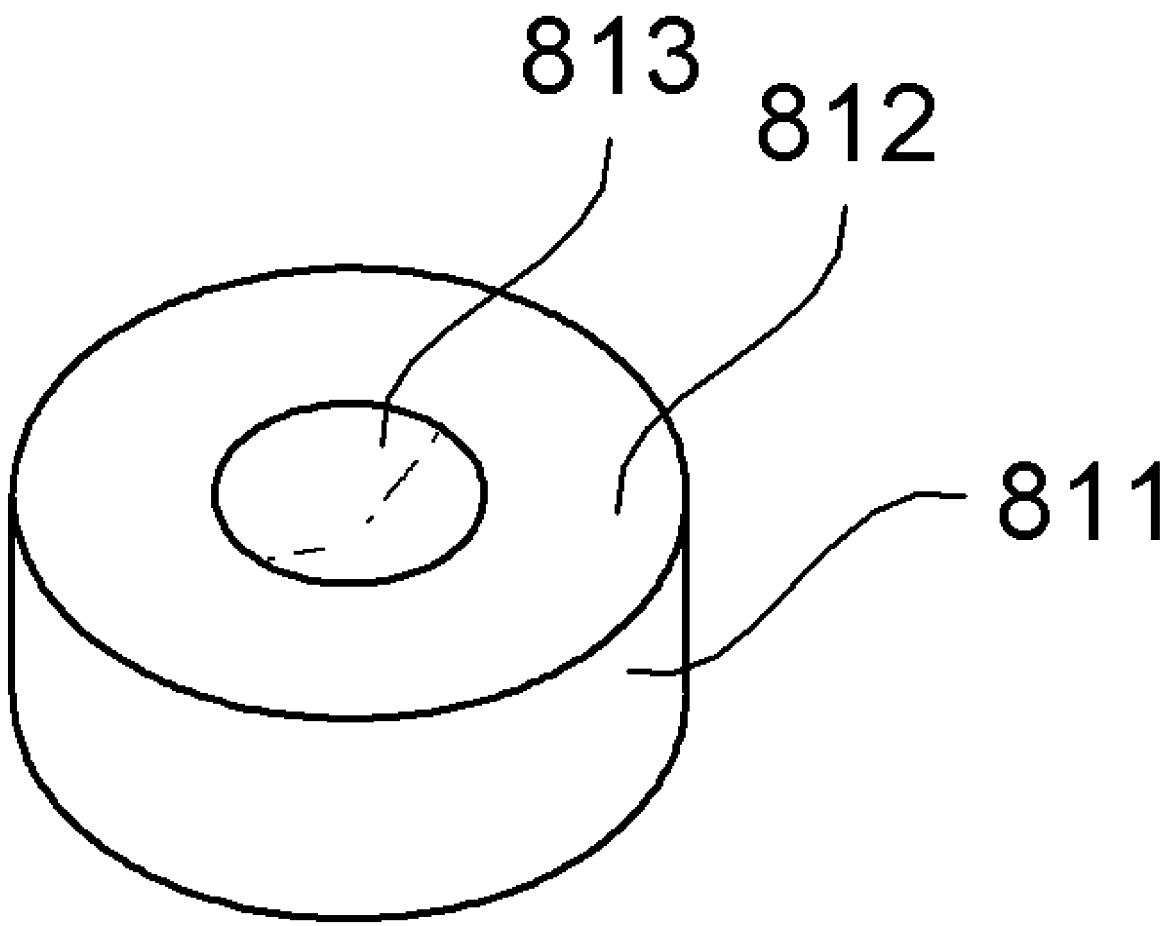
FIG. 30 is a perspective view illustrating a sealing member.
Figure 31:
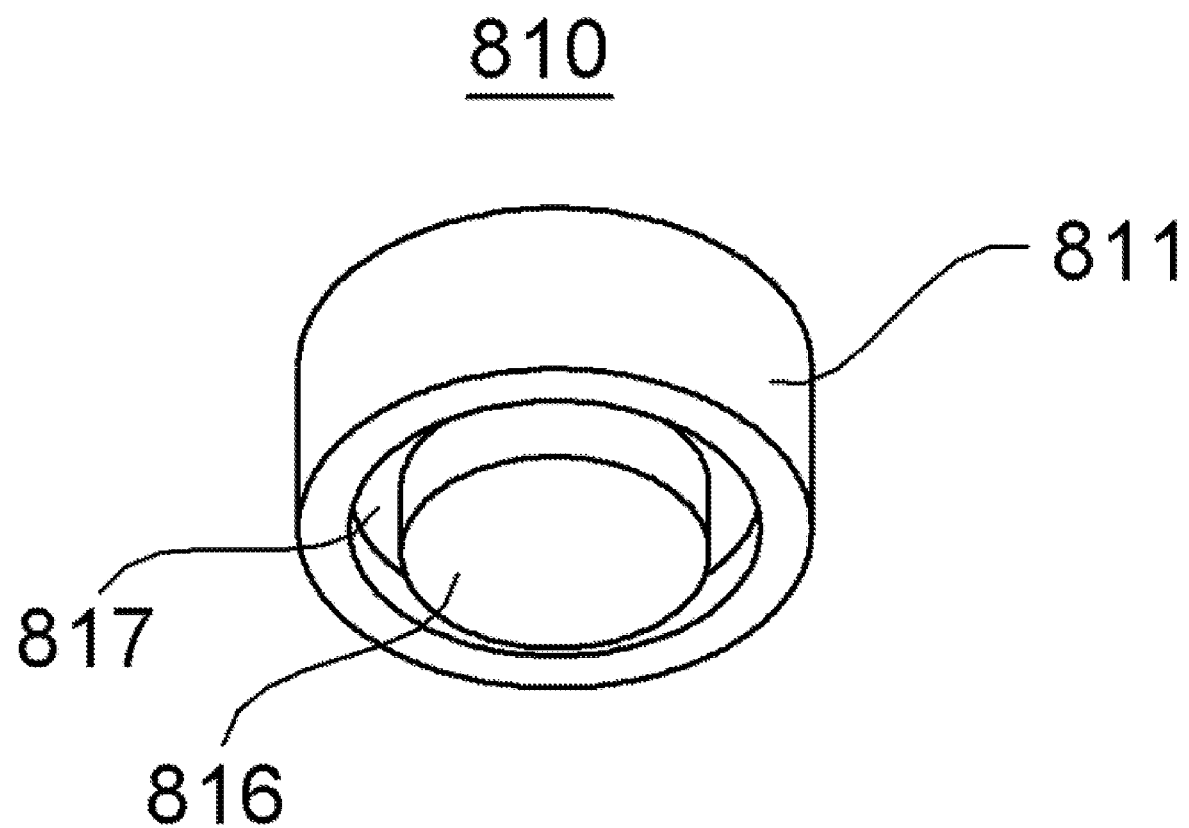
FIG. 31 is a bottom view illustrating the sealing member.

FIG. 30 is a perspective view illustrating the sealing member 810, and FIG. 31 is a bottom view illustrating the sealing member 810.

Referring to FIGS. 29 to 31, the sealing member 810 seals a space between the first member 820 and the deaeration pipe 130. The sealing member 810 may be disposed to cover the top end of the deaeration pipe 130. The sealing member 810 directly opens or closes the hole 140. A concave groove 813 may be disposed at a top surface 812 of the sealing member 810. The groove 813 may have a conical shape. Also, an annular second groove 817 may be disposed at a bottom surface of the sealing member 810. The annular second groove 817 is configured to be coupled with the top surface of the deaeration pipe 130. The annular second groove 817 enhances a coupling property and adhesion between the deaeration pipe 130 and the sealing member 810.

Figure 32:
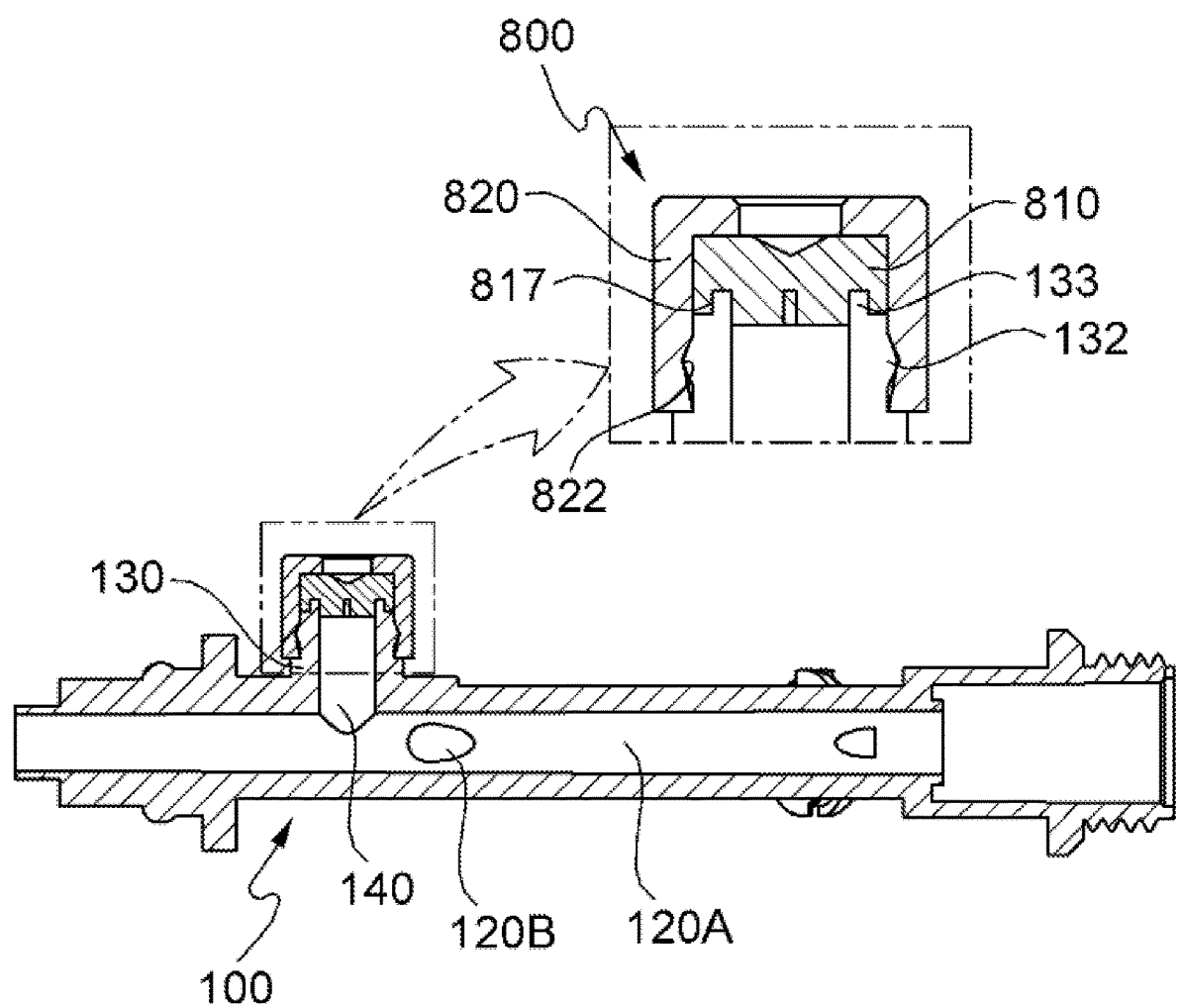
FIG. 32 is a side cross-sectional view illustrating the opening and closing portion shown in FIG. 28.

FIG. 32 is a side cross-sectional view illustrating the opening and closing portion 800 shown in FIG. 28.

Referring to FIGS. 29 to 32, the deaeration pipe 130 may include a first protrusion 132 and a second protrusion 133. The first protrusion 132 protrudes from the side surface of the deaeration pipe 130. The second protrusion 133 protrudes from the top surface of the deaeration pipe 130. The first member 820 may include a first groove 822 concavely formed at an inner surface. The first protrusion 132 is disposed in the first groove 822. The second protrusion 133 is disposed in the second groove 817.

The first member 820 is coupled with the deaeration pipe 130 while coming into contact with the sealing member 810 and fixes the sealing member 810 to the deaeration pipe 130. The hole 140 is disposed at a center of the first member 820. While the first member 820 is coupled with the deaeration pipe 130, the hole 140 is aligned with the groove 813 or a bottom surface 816 of the sealing member 810. The through hole 821 exposes the sealing member 810.

Figure 33:
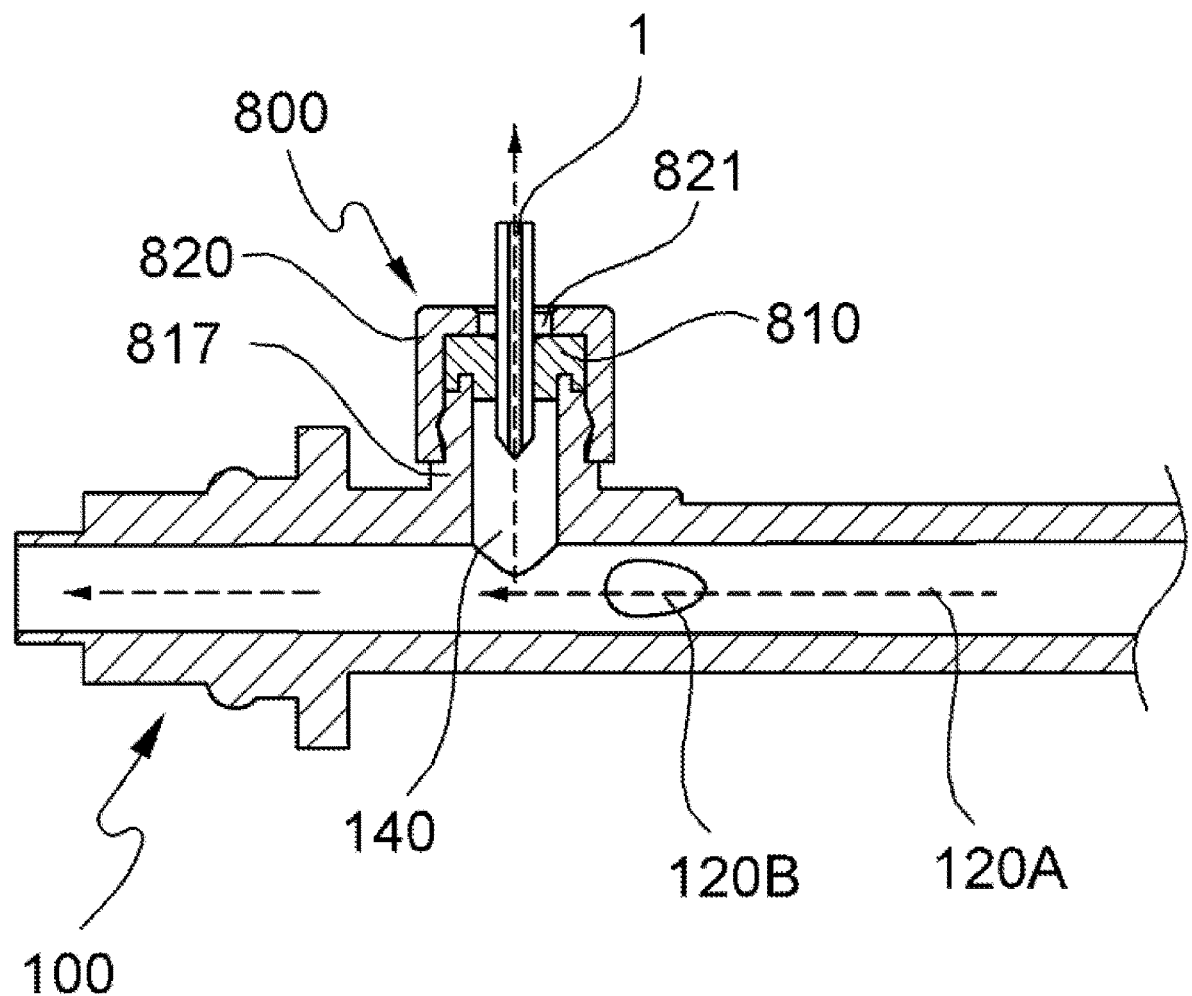
FIG. 33 is a view illustrating a state in which the opening and closing portion shown in FIG. 28 is opened by a user's tool (needle).

FIG. 33 is a view illustrating a state in which the opening and closing portion 800 shown in FIG. 28 is opened by a user's tool (needle).

Referring to FIG. 33, when bubbles in the channel 120 are seen during treatment, the user inserts a needle of a syringe into the sealing member 810. The needle passes through the sealing member 810. When the needle passes through the sealing member 810, the needle communicates with the hole 140. When the user pulls a plunger of the syringe, the bubbles existing in the hole 140 are collected at the syringe through the needle and removed. The sealing member 810 is formed of an elastic material. When the needle is removed from the sealing member 810, an area of the sealing member 810, which is perforated by the needle, is restored by elasticity such that the hole 140 is sealed.

The hemostasis valve device according to one exemplary embodiment of the present invention has been described above in detail with reference to the attached drawings.

According to the embodiments, an advantageous effect of preventing air flowing into blood vessels may be provided.

According to the embodiments, an advantageous effect of removing bubbles using a simple operation may be provided.

According to the embodiments, an advantageous effect that a practitioner can remove bubbles single-handed may be provided.

According to the embodiments, an advantageous effect that additional devices or treatments are not necessary for removing bubbles may be provided.

According to the embodiments, an advantageous effect of removing not only bubbles caused by introduction of catheters but also bubbles caused by injection of medications may be provided.

It should be noted that the above-described one embodiment of the present invention is merely an example in all aspects and is not intended to be limitative, and the scope of the present invention will be defined by the following claims rather than the above detailed description. Also, it should be interpreted that all changeable or modifiable shapes derived from the meaning and scope of the claims and equivalents thereof are included in the scope of the present invention.

What is claimed is:

1. A hemostasis valve device comprising:
a connector comprising a first channel;
a holder disposed at a first end of the connector and configured to communicate with the first channel; and
a valve portion disposed at a second end of the connector and configured to selectively open or close the first channel,
wherein the connector comprises a first pipe including the first channel and a second pipe which diverges from a first point of the first pipe and includes a second channel configured to communicate with the first channel,
wherein the first pipe comprises a hole which allows the first channel to communicate with the outside,
wherein the hemostasis valve device further comprises an opening and closing portion disposed at the first pipe and configured to selectively open or close the hole,
wherein the opening and closing portion comprises a first member movable relative to the first pipe, and a sealing member adjacent to the first member and configured to cover the hole,
wherein the first member includes a body and a tube extending from a surface of the body towards the sealing member and in communication with the outside, and
wherein the hole is disposed between the first end and the first point.

2. The hemostasis valve device of claim 1, wherein the connector comprises a deaeration pipe including the hole,
wherein the sealing member is disposed between the first member and the deaeration pipe,
wherein the first member is coupled with the deaeration pipe,
wherein the sealing member comprises an incised portion, and
wherein the tube communicates with the hole while passing through the incised portion.

3. The hemostasis valve device of claim 2, wherein the hole is a first hole,
wherein the opening and closing portion further comprises:
a second member which is coupled with the deaeration pipe and includes
a second hole through which the tube passes; and
an elastic member,
wherein the first member is coupled with the second member to be movable relative to the first pipe,
wherein the second member is disposed between the first member and the elastic member, and
wherein the elastic member is disposed between the first member and the second member.

4. The hemostasis valve device of claim 3, wherein the body of the first member comprises a top surface and a side surface, and
wherein the side surface comprises a connection hole which connects with the tube.

5. A hemostasis valve device comprising:
a connector which comprises a first pipe and a second pipe diverging from a first point of the first pipe;
a holder disposed at a first end of the first pipe; and
a valve portion disposed at a second end of the first pipe,
wherein the first pipe comprises a deaeration pipe in which a hole is disposed,
wherein the hemostasis valve device further comprises an opening and closing portion disposed at the deaeration pipe and configured to selectively open or close the hole,
wherein the opening and closing portion comprises a first member movable relative to the first pipe, and a sealing member adjacent to the first member and configured to cover the hole,
wherein the first member includes a body and a tube extending from a surface of the body towards the sealing member and in communication with the outside, and
wherein the hole is disposed between the first end and the first point.

6. The hemostasis valve device of claim 5,
wherein the sealing member is disposed between the first member and the deaeration pipe,
wherein the first member is coupled with the deaeration pipe,
wherein the sealing member comprises an incised portion, and
wherein the tube communicates with the hole while passing through the incised portion.

7. The hemostasis valve device of claim 6, wherein the body of the first member comprises a top surface and a side surface, and
wherein the side surface comprises a connection hole which connects with the tube.

8. The hemostasis valve device of claim 7, wherein the hole is a first hole,
wherein the opening and closing portion further comprises:
a second member which is coupled with the deaeration pipe and includes
a second hole through which the tube passes; and
an elastic member, wherein the first member is coupled with the second member to be movable relative to the first pipe,
wherein the second member is disposed between the first member and the elastic member, and
wherein the elastic member is disposed between the first member and the second member.

* * * * *